United States Patent
Phipps et al.

(10) Patent No.: US 9,012,439 B2
(45) Date of Patent: Apr. 21, 2015

(54) USE OF ELECTROPHILIC COMPOUNDS FOR INDUCING PLATELET PRODUCTION OR MAINTAINING PLATELET FUNCTION

(75) Inventors: Richard P. Phipps, Pittsford, NY (US); Jamie O'Brien, Fairport, NY (US)

(73) Assignee: University of Rochester, Rochester, NY (US)

( * ) Notice: Subject to any disclaimer, the term of this patent is extended or adjusted under 35 U.S.C. 154(b) by 785 days.

(21) Appl. No.: 12/738,949

(22) PCT Filed: Oct. 29, 2008

(86) PCT No.: PCT/US2008/081565
§ 371 (c)(1),
(2), (4) Date: Jul. 6, 2010

(87) PCT Pub. No.: WO2009/058849
PCT Pub. Date: May 7, 2009

(65) Prior Publication Data
US 2011/0027223 A1    Feb. 3, 2011

Related U.S. Application Data

(60) Provisional application No. 60/983,352, filed on Oct. 29, 2007.

(51) Int. Cl.
*A61K 31/56*    (2006.01)
*A61K 31/557*    (2006.01)

(52) U.S. Cl.
CPC ............... *A61K 31/56* (2013.01); *A61K 31/557* (2013.01)

(58) Field of Classification Search
None
See application file for complete search history.

(56) References Cited

U.S. PATENT DOCUMENTS

| | | | |
|---|---|---|---|
| 6,974,801 B2 | 12/2005 | Honda et al. | |
| 7,176,237 B2 | 2/2007 | Honda et al. | |
| 2002/0037290 A1 | 3/2002 | Armen | |
| 2002/0042535 A1 | 4/2002 | Gribble et al. | |
| 2003/0232786 A1 | 12/2003 | Honda et al. | |
| 2004/0002463 A1 | 1/2004 | Honda et al. | |
| 2004/0087560 A1 | 5/2004 | Hajduch et al. | |
| 2004/0266868 A1 | 12/2004 | Hajduch et al. | |
| 2005/0288363 A1 | 12/2005 | Gribble et al. | |
| 2006/0160890 A1 | 7/2006 | Hajduch et al. | |
| 2007/0135382 A1 | 6/2007 | Phipps et al. | |
| 2009/0048205 A1* | 2/2009 | Meyer et al. | 514/49 |

FOREIGN PATENT DOCUMENTS

WO    2008064132 A2    5/2008

OTHER PUBLICATIONS

Vippagunta et al., Advanced drug delivery Reviews, (2001), 48, pp. 3-26.*
McDonald, T.P., Experimental Hematology, (1988), 16(3), pp. 201-5 (abstract).*
Satoh et al., Journal of Neurochemistry, 2008, vol. 104, pp. 1115-1131.*
PCT International Search Report and Written Opinion PCT/US2008/081565 Jan. 22, 2009.
Honda et al., "Design and Synthesis of 2-Cyano-3,12-Dioxoolean-1,9-Dien-28-Acid, a Novel and Highly Active Inhibitor of Nitric Oxide Production in Mouse Macrophages," Biorg. Med. Chem. Lett. 8:2711-2714 (1998).
Honda et al., "Novel Synthetic Oleanane and Ursane Triterpenoids with Various Enone Functionalities in Ring A as Inhibitors of Nitric Oxide Production in Mouse Macrophages," J. Med. Chem. 43:1866-1877 (2000).
Honda et al., "Synthetic Oleanane and Ursane Triterpenoids with Modified Rings A and C: A Series of Highly Active Inhibitors of Nitric Oxide Production in Mouse Macrophages," J. Med. Chem. 43:4233-4246 (2000).
Honda et al., "A Novel Dicyanotriterpenoid, 2-Cyano-3,12-Dioxooleana-1,9(11)-Dien-28-onitrile, Active at Picomolar Concentrations for Inhibition of Nitric Oxide Production," Biorg. Med. Chem. Lett. 12:1027-1030 (2002).
Dinkova-Kostora et al., "Extremely Potent Triterpenoid Inducers of the Phase 2 Response: Correlations of Protection Against Oxidant and Inflammatory Stress," Proc. Natl. Acad. Sci. USA 102(12):4584-4589 (2005).
Place et al., "The Novel Synthetic Triterpenoid, CDDO-Imidazolide, Inhibits Inflammatory Response and Tumor Growth in Vivo," Clin. Cancer Res. 9:2798-2806 (2003).
O'Brien, J. and Phipps, R.P., "Induction of Platelet Formation by 15-deoxy-prostagandin J2 in a Megakaryoblastic Cell Line," 8th Annual Winter Eicosanoids Conference, Baltimore, MD, Mar. 13-16, 2006 (abstract only).

* cited by examiner

*Primary Examiner* — Savitha Rao
*Assistant Examiner* — Gregg Polansky
(74) *Attorney, Agent, or Firm* — LeClairRyan, a Professional Corporation

(57) ABSTRACT

The present invention is directed to a method of inducing platelet production that includes contacting a megakaryocyte with an electrophilic compound under conditions effective to induce platelet production by the contacting megakaryocyte. Methods of treating a patient for low platelet levels, increasing the circulating half-life of platelets, and improving the quality (activity) of platelets are also disclosed herein, which involve administering the electrophilic compound to a patient an effective amount to achieve the desired effect. Pharmaceutical compositions and therapeutic systems are also disclosed for carrying out these therapeutic treatments.

25 Claims, 15 Drawing Sheets

Figure 1F Untreated

Figure 1G 15d-PGJ$_2$

Untreated

15d-PGJ$_2$

Figure 1H  Figure 1I

USE OF ELECTROPHILIC COMPOUNDS FOR INDUCING PLATELET PRODUCTION OR MAINTAINING PLATELET FUNCTION

This application is a national stage application under 35 U.S.C. 371 of PCT/US2008/081565, filed Oct. 29, 2008, and claims the benefit of U.S. Provisional Patent Application Ser. No. 60/983,352, filed Oct. 29, 2007, which is hereby incorporated by reference in its entirety.

This invention was made with government support under grant HL 078604 awarded by the National Institutes of Health. The government has certain rights in the invention.

FIELD OF THE INVENTION

The present invention is directed to the use of electrophilic compounds for inducing platelet production or maintaining platelet function, and therapeutic compositions, systems, and treatments for conditions invention involving low platelet counts (thrombocytopenia).

BACKGROUND OF THE INVENTION

Platelets initiate clot formation and have important roles in both innate and adaptive immunity (Henn et al., "CD40 Ligand on Activated Platelets Triggers an Inflammatory Reaction of Endothelial Cells," *Nature* 391:591-594 (1998) and Wagner et al., "Platelets in Inflammation and Thrombosis," *Arterioscler Thromb Vasc Biol* 23:2131-2137 (2003)). Loss of platelets either by their destruction in the periphery or their reduced production can occur in diseases such as immune thrombocytopenic purpura, thrombotic thrombocytopenic purpura, human immunodeficiency virus (HIV) infection, aplastic anemia, and acute respiratory distress syndrome and in about 1-5% of people receiving heparin therapy (Cines et al., "Heparin-induced Thrombocytopenia: An Autoimmune Disorder Regulated Through Dynamic Autoantigen Assembly/Disassembly," *J Clin Apher* 22:31-36 (2007)). In addition, cancer chemotherapy and radiation therapy are two of the most common causes of thrombocytopenia. Currently, platelet transfusions are the "gold-standard" for treating the life-threatening complications of thrombocytopenia. However, platelet transfusions increase the risk of inflammation and disease transmission, are costly and not always readily available (Blumberg et al., "An Association of Soluble CD40 Ligand (CD154) with Adverse Reactions to Platelet Transfusions," *Transfusion* 46:1813-1821 (2006); Kaufman et al., "Release of Biologically Active CD154 During Collection and Storage of Platelet Concentrates Prepared for Transfusion," *J Thromb Haemost* 5:788-796 (2007)). A catastrophic event such as mass radiation exposure would leave many victims without treatment. Currently, recombinant human interleukin (IL-)11, the only clinically approved drug for treating thrombocytopenia, is used as an alternative to platelet transfusions to modestly raise platelet counts (Bhatia et al., "The Role of Interleukin-11 to Prevent Chemotherapy-induced Thrombocytopenia in Patients with Solid Tumors, Lymphoma, Acute Myeloid Leukemia and Bone Marrow Failure Syndromes," *Leuk Lymphoma* 48:9-15 (2007)). Therefore, there remains a need for more efficacious and readily available treatments to increase platelet number.

Platelets are derived from megakaryocytes, which reside in the bone marrow (Patel et al., "The Biogenesis of Platelets from Megakaryocyte Proplatelets," *J Clin Invest* 115:3348-3354 (2005)). During megakaryocyte maturation, the polyploid cell undergoes a complex process of cytoskeletal rearrangement, followed by proplatelet elongation, and the release of cytoplasmic fragments as circulating platelets (Italiano et al., "Blood Platelets are Assembled Principally at the Ends of Proplatelet Processes Produced by Differentiated Megakaryocytes,"*J Cell Biol* 147:1299-1312 (1999); Kaushansky, "Historical Review: Megakaryopoiesis and Thrombopoiesis," *Blood* 111:981-986 (2008)). Proteomic studies have revealed that both megakaryocytes and platelets contain proteins of unknown function. It has been reported that the ligand-activated transcription factor, peroxisome proliferator-activated receptor gamma (PPARγ), is present in both megakaryocytes and platelets (Akbiyik et al., "Human Bone Marrow Megakaryocytes and Platelets Express PPARγ, and PPARγ Agonists Blunt Platelet Release of CD40 Ligand and Thromboxanes," *Blood* 104:1361-1368 (2004)). PPARγ functions as a heterodimer with the Retinoid X Receptor (RXR) to regulate adipogenesis, glucose metabolism, and inflammation (Schoonjans et al., "The Peroxisome Proliferator Activated Receptors (PPARS) and Their Effects on Lipid Metabolism and Adipocyte Differentiation," *Biochim Biophys Acta* 1302:93-109 (1996); Kliewer et al., "Convergence of 9-cis Retinoic Acid and Peroxisome Proliferator Signalling Pathways Through Heterodimer Formation of Their Receptors," *Nature* 358:771-774 (1992)). It has also been shown that the PPARγ ligands rosiglitazone and 15d-PGJ$_2$ dampen thrombin-induced human platelet activation and aggregation (Akbiyik et al., "Human Bone Marrow Megakaryocytes and Platelets Express PPARγ, and PPARγ Agonists Blunt Platelet Release of CD40 Ligand and Thromboxanes," *Blood* 104: 1361-1368 (2004)). Importantly, it was recently determined that PPARγ is also found in platelet microparticles released during activation (Ray et al., "Peroxisome Proliferator-activated Receptor Gamma and Retinoid X Receptor Transcription Factors are Released from Activated Human Platelets and Shed in Microparticles," *Thromb Haemost* 99:86-95 (2008)). Initially, it was believed that PPARγ ligands would blunt the activity of platelets treated with PPARγ ligands by minimizing unwanted pro-inflammatory and/or prothrombotic responses by the platelets, and platelets produced by megakaryocytes treated with PPARγ ligands would likewise exhibit diminished pro-inflammatory and/or prothrombotic response (PCT Publ. WO 2005/041872 to Phipps et al.).

It would be desirable to identify classes of compounds that can be used to improve the production of platelets by megakaryocytes, and thereby afford improved therapeutic treatment of conditions that involve low platelet count. The present invention is directed to overcoming these and other deficiencies in the art.

SUMMARY OF THE INVENTION

A first aspect of the present invention relates to a method of inducing platelet production that includes contacting a megakaryocyte with an electrophilic compound under conditions effective to induce platelet production by the contacted megakaryocyte.

A second aspect of the present invention relates to a method of treating a patient for low platelet levels (thrombocytopenia) that includes: administering to a patient having low platelet levels an effective amount of an electrophilic compound that is suitable to cause an increase in platelet production by megakaryocytes.

A third aspect of the present invention relates to a pharmaceutical composition or therapeutic system that includes an agent that increases megakaryocyte production and an electrophilic compound capable of inducing platelet production by megakaryocytes.

A fourth aspect of the present invention relates to a method of increasing the circulating half-life of platelets that includes administering to a patient an effective amount of an electrophilic compound that is suitable to increase the circulating half-life of platelets.

A fifth aspect of the present invention relates to a method of improving the quality (activity) of platelets that includes administering to a patient an effective amount of an electrophilic compound that is suitable to improve the quality (activity) of platelets.

A sixth aspect of the present invention relates to use of an electrophilic compound in an amount effective to treat thrombocytopenia in a patient or use of an electrophilic compound in the manufacture of a medicament for the treatment of thrombocytopenia.

Thrombocytopenia is a critical problem that occurs in many hematological diseases, as well as after cancer therapy and radiation exposure. Platelet transfusion is the most commonly used therapy, but has limitations of alloimmunization, availability, and expense. Thus, the development of safe, small molecules to enhance platelet production would be advantageous for the treatment of thrombocytopenia. The examples presented herein demonstrate that two distinct classes of electrophilic compounds, prostaglandins and tri-terpenoids, can promote platelet formation. 15-deoxy-$\Delta^{12,14}$ prostaglandin $J_2$ (15d-$PGJ_2$) increases Meg-01 maturation and platelet production. 15d-$PGJ_2$ also promotes platelet formation from culture-derived mouse and human megakaryocytes and accelerates platelet recovery after in vivo radiation-induced bone marrow injury. Interestingly, the platelet-enhancing effects of 15d-$PGJ_2$ in Meg-01 cells are independent of PPARγ but dependent on reactive oxygen species (ROS) accumulation; treatment with antioxidants such as glutathione ethyl ester (GSH-EE) or N-acetylcysteine (NAC) attenuate 15d-$PGJ_2$-induced platelet production. The tri-terpenoid methyl-2-cyano-3,12-dioxooleana-1,9-dien-28-oate (CDDO-Me) was also shown to improve platelet production in animal studies. Thus, the present invention demonstrates that megakaryocyte redox status plays an important role in platelet generation and that small electrophilic molecules are effective for improving platelet numbers in thrombocytopenic patients.

BRIEF DESCRIPTION OF THE DRAWINGS

FIGS. 1A-I show that 15d-$PGJ_2$ enhances platelet production from megakaryoblast cell lines. FIG. 1A shows that one ×10$^6$ Meg-01, M07e, or Dami cells were treated with 15d-$PGJ_2$ (10 μM) for 24 h. 15d-$PGJ_2$ increases platelet production in Meg-01, M07e, and Dami cells after 24 h. FIG. 1B shows that one ×10$^6$ Meg-01 cells were treated with prostaglandins for 24 h. 15d-$PGJ_2$ dose-dependently increased platelet production in Meg-01 cells after 24 h, unlike $PGE_2$ (10 μM), $PGI_2$ (10 μM), and $PGF_{2\alpha}$ (10 μM). FIG. 1C shows that 92% of the Meg-01-derived platelets expressed the platelet surface marker CD61. Isotype control is shown by the left histogram. Results are presented as mean±SD (P<0.05). FIG. 1D shows forward and side scatter plots illustrating that platelets produced from untreated and 15d-$PGJ_2$-treated (10 μM for 24 h) Meg-01 cells mimic freshly isolated human platelets in their ability to undergo shape change with 15 min of collagen treatment (10 μg/mL). 87% of human platelets, 87% of Meg-01-derived platelets, and 68% of the platelets produced from 15d-$PGJ_2$-treated Meg-01 cells decreased their size (forward scatter) and increased their granularity (side scatter) in response to collagen. FIG. 1E depicts histogram plots showing that Meg-01-derived platelets are similar to normal human platelets in their ability to undergo annexin V binding both in the presence and absence of collagen. Values are geometric mean fluorescence intensity. FIG. 1F shows Meg-01 cells that were untreated or treated with DMSO (vehicle) or 15d-$PGJ_2$ (10 μM) for 2 h. Phalloidin staining of f-actin fibers shown by fluorescence microscopy in an untreated cell. Note DAPI stained nucleus (n) and smooth rounded cell surface. FIG. 1G shows phalloidin staining of f-actin fibers shown by fluorescence microscopy. Left picture shows heavy phalloidin staining of organized f-actin bundles in a cell treated with 10 μM of 15d-$PGJ_2$ for 2 h. Right picture shows enlarged (40×) section highlighting membrane demarcations. Arrows show heavy phalloidin staining of f-actin bundles. FIG. 1H shows Meg-01 cells that were untreated or treated with 10 μM of 15d-$PGJ_2$ for 24 h. Transmission electron microscopy (TEM) showing an untreated cell. Note smooth round nucleus (n) and the absence of granules. FIG. 1I depicts a left TEM picture which shows a cell treated with 10 μM of 15d-$PGJ_2$ for 24 h. Note horseshoe-shaped nucleus (n), granule content (g), and cytoplasmic extensions (c). Right picture shows enlarged section highlighting cytoplasmic extensions.

FIG. 2A shows the percentage of total cells from bone marrow cultures that are CD61+ platelets. Bone marrow cultures were treated with either vehicle or 15d-$PGJ_2$. Results are presented as mean±SD (P<0.01). FIG. 2B shows platelets that were isolated from other cells in culture by gradient centrifugation from mouse bone marrow cultures treated with 15d-$PGJ_2$. Left plot shows the forward and side scatter of untreated platelets. Right plot shows the forward and side scatter of platelets treated with collagen (10 μg/mL for 15 min). Note the decrease in size and increase in granularity. FIG. 2C is a histogram showing the upregulation of surface CD41 with collagen treatment. Values are a measure of geometric mean fluorescence intensity. FIG. 2D shows scanning electron microscopy of two culture-derived mouse platelets spread on a fibrinogen coated slide. The left picture of FIG. 2E shows microscopy of a mouse megakaryocyte cultured in the absence of 15d-$PGJ_2$. Note the smooth surface. The right picture of FIG. 2E shows microscopy of a mouse megakaryocyte cultured in the presence of 15d-$PGJ_2$. Note the ruffled surface characteristic of morphological changes that promote proplatelet formation.

FIG. 3A shows that 15d-$PGJ_2$ increases the number of platelets derived from primary human megakaryocytes. Results are presented as mean±SD (P<0.01). FIG. 3B shows platelets that were isolated by gradient centrifugation from CD61+ cell cultures treated with 15d-$PGJ_2$. Left plot shows the forward and side scatter of untreated platelets. Right plot shows the forward and side scatter of platelets treated with collagen (10 μg/mL for 15 min). Note the decrease in size and increase in granularity. FIG. 3C shows the upregulation of surface CD61 with collagen treatment. Values are a measure of geometric mean fluorescence intensity. FIG. 3D is an SEM showing a culture-derived human platelet spread on a fibrinogen coated slide. The left picture of FIG. 3E shows microscopy of a human megakaryocyte cultured in the absence of 15d-PGJ$_2$. Middle picture shows microscopy of a human megakaryocyte cultured in the presence of 15d-PGJ$_2$. Arrows indicate proplatelets. Far right picture shows magnification of proplatelet extensions.

FIG. 4A shows cells that were transiently transfected with a PPRE-luciferase construct and treated with either 10 μM 15d-PGJ$_2$, 9,10 dihydro-15d-PGJ$_2$, or rosiglitazone. Twenty-four hours after ligand treatment, a luciferase assay was performed. Cells treated with PPARγ ligands had increased luciferase activity compared to the untreated cells. FIG. 4B shows Meg-01 cells that were treated with DMSO (vehicle control), or with 10 μM rosiglitazone, 15d-PGD$_2$, 9,10 dihydro-15d-PGJ$_2$, 15d-PGJ$_2$, or PGJ$_2$ and platelet number was assessed by flow cytometry. Results are presented as mean±SD (P<0.01). FIG. 4C is a Western blot showing that cells infected with PPARγ-siRNA have 66% less PPARγ protein compared to cells infected with the control (con) virus. FIG. 4D shows cells either infected with lentivirus PPARγ-siRNA or pre-treated for 2 h with 100 nM GW9662, an irreversible PPARγ antagonist, were treated with 15d-PGJ$_2$ for 24 h. Platelet production was assessed by flow cytometry. Results are presented as mean±SD (P<0.01, n=3).

FIG. 5A shows one x10$^6$ Meg-01 cells were untreated or treated with DMSO, 9,10 dihydro-15d-PGJ$_2$, 15d-PGJ$_2$, PGJ$_2$, or 15d-PGD$_2$, at a concentrations up to 10 μM, for 1 h and 6 h. Cells were harvested and carboxy-H$_2$DCFDA was added for 30 min and the cells were analyzed by flow cytometry. The percent of ROS-positive cells is shown. FIG. 5B shows Meg-01 cells were exposed to DMSO, or to 10 μM 15d-PGD$_2$, 9,10 dihydro-15-PGJ$_2$, 15d-PGJ$_2$, or PGJ$_2$ for 1 or 6 h. Cells were harvested and MitoSOX red was added for 15 min and the cells were analyzed by flow cytometry. The percent of ROS-positive cells is shown. FIG. 5C shows one x10$^6$ primary human megakaryocytes were untreated or treated with DMSO, 9,10 dihydro-15d-PGJ$_2$, 15d-PGJ$_2$ at concentrations up to 10 μM, for 1 h and 6 h. Cells were harvested and carboxy-H$_2$DCFDA was added for 30 min or MitoSOX red was added for 15 min and the cells were analyzed by flow cytometry. The percentage of ROS-positive cells is shown. FIG. 5D shows cells that were pretreated with either 1 mM NAC or 5 mM GSH-EE for 2 h followed by treatment with 15d-PGJ$_2$ (10 μM) or a co-treatment of NAC (1 mM) and 15d-PGJ$_2$ (10 μM) for 24 h. Top bar graph shows the effects of antioxidants on platelet production from Meg-01 cells and bottom bar graph shows the effects of antioxidants on platelet production from primary human megakaryocytes.

FIG. 6A shows Meg-01 cells that were treated with vehicle or 15d-PGJ$_2$ (10 μM) for 24, 48, or 72 h. Left histogram shows vehicle-treated Meg-01 cells (72 h). Right histogram shows 15d-PGJ$_2$-treated Meg-01 cells (72 h). Bar graph demonstrates that by 72 h Meg-01 cells in the presence of 15d-PGJ$_2$ exhibit higher DNA contents when compared to Meg-01 cells in the presence of vehicle. Results are presented as mean±SD (P<0.05). FIG. 6B shows primary mouse megakaryocytes that were treated with vehicle or 15d-PGJ$_2$ (10 μM) for 24 h. Left histogram shows vehicle-treated cells (24 h). Right histogram shows 15d-PGJ$_2$-treated cells (24 h). Bar graph demonstrates that by 24 h cells in the presence of 15d-PGJ$_2$ exhibit higher DNA content when compared to cells in the presence of vehicle. Results are presented as mean±SD (P<0.05). Top bar graph of FIG. 6C shows the number of Meg-CFC colonies. Bottom bar graph of FIG. 6C shows the size of Meg-CFC colonies. Results are presented as mean±SD (P<0.05). FIG. 6D shows the percentage of megakaryocytes exhibiting proplatelet extensions. Results are presented as mean±SD (P<0.05). FIG. 6E shows immunohistochemical GP1bβ and GPV staining of megakaryocyte progenitor-derived colonies. Left picture shows colonies grown from bone marrow of vehicle-treated mice. Middle picture shows colonies grown from bone marrow of 15d-PGJ$_2$-treated mice. Note proplatelet extensions (p). Far right picture shows a magnification of the proplatelet extensions.

FIG. 7A shows C57BL/6 mice that were injected IV with 1 mg/kg 15d-PGJ$_2$ for four consecutive days. Platelet number was measured on d 4, d 10, and d 15. There is a significant increase in the levels of circulating platelets on d 4 in mice treated with 15d-PGD$_2$. Results are presented as mean±SD (P<0.01) (n=4). FIG. 7B shows C57BL/6 mice that were exposed to 5 Gy of total body ionizing irradiation on d 0 and on the following four consecutive days, were injected IV with 1 mg/kg 15d-PGJ$_2$. Platelet number was measured on d 10, d 22 and d 31. There is a significant increase in the levels of circulating platelets on d 22 and d 31 in mice treated with 15d-PGJ$_2$. Results are presented as mean±SD (P<0.01) (n=8).

DETAILED DESCRIPTION OF THE INVENTION

Figure 1A:
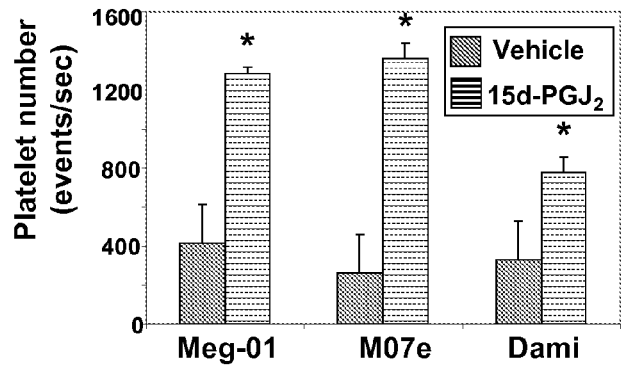

The present invention demonstrates that megakaryocyte redox status plays an important role in platelet generation and that small electrophilic molecules may have clinical efficacy for improving platelet numbers in thrombocytopenic patients.

According to one aspect, the present invention relates to a method of inducing platelet production that includes contacting a megakaryocyte with an electrophilic compound under conditions effective to induce platelet production by the contacted megakaryocyte. As described below, this method can be carried out ex vivo or in vivo. For ex vivo treatment, the exposure of megakaryocytes is carried out outside the body, and then either the treated megakaryocytes are introduced or re-introduced to the patient or the platelets produced thereby are introduced to the patient. Alternatively, the megakaryocytes can be contacted in vivo by directly administering to a patient in need thereof an effective amount of an electrophilic compound (that is suitable to cause an increase in platelet production by megakaryocytes).

As used herein, the patient to be treated can be any mammal that has low platelet count or thrombocytopenia. Thus, the present invention contemplates both therapeutic treatment of humans as well as therapeutic treatment of non-humans for veterinary purposes.

Thrombocytopenia is the term for a reduced platelet (thrombocyte) count. It happens when platelets are lost from the circulation faster than they can be replaced from the bone marrow where they are made. Patients having a low platelet count are susceptible to problems with clot formation. At less than 80-100 million platelets per ml, an increased risk of excessive bleeding exists and should be treated.

Thrombocytopenia can be caused by any of a number of diseases including, without limitation, problems associated with megakaryocyte maturation (often associated with bone marrow problems such as acute leukemias and lymphomas); impaired platelet production caused by viral infections such as HIV, metabolic disorders such as shortage of vitamin B12 or folic acid, kidney failure, alcohol, etc.; an abnormality of the bone marrow called myelodysplasia; immune thrombocytopenic purpura; thrombotic thrombocytopenic purpura; aplastic anemia; and acute respiratory distress syndrome. Thrombocytopenia can also be a side-effect of other therapeutic regimen, including heparin therapy (Cines et al., "Heparin-induced Thrombocytopenia: An Autoimmune Disorder Regulated Through Dynamic Autoantigen Assembly/Disassembly," *J Clin Apher* 22:31-36 (2007), which is hereby incorporated by reference in its entirety), and cancer chemotherapy and radiation therapy, which represent two of the most common causes of thrombocytopenia.

According to one embodiment, the thrombocytopenia to be treated in accordance with the present invention is not a side-effect of chemotherapy, and therefore the electrophilic compounds used in accordance with the present invention are intended for purposes other than chemotherapeutic treatment of a cancerous condition. The use of the electrophilic compounds to treat thrombocytopenia that is a side-effect of radiation therapy and/or heparin therapy is contemplated in this embodiment.

According to another embodiment, the thrombocytopenia to be treated in accordance with the present invention is a side-effect of chemotherapy, but the chemotherapeutic agent that is administered to the patient is not a tri-terpenoid derivative of oleanolic, ursolic, or betulinic acids, and not a tricyclic bis-enone derivative. Use of the electrophilic compounds described herein in conjunction with chemotherapeutic agents, therefore, is specifically contemplated.

One class of suitable electrophilic compounds includes, without limitation, prostaglandins (PG) and prostaglandin derivatives such as $PGD_2$, $PGJ_2$ and its metabolite 15d-$PGJ_2$, or any combination thereof. $PGJ_2$ and 15d-$PGJ_2$ are natural PPARγ ligands that are biologically active metabolites of $PGD_2$ (Forman et al., "15-Deoxy-delta 12,14-prostaglandin J2 is a Ligand for the Adipocyte Determination Factor PPARγ," *Cell* 83:803-812 (1995); Fukushima M., "Biological Activities and Mechanisms of Action of PGJ2 and Related Compounds: An Update," *Prostaglandins Leukot Essent Fatty Acids* 47(1):1-12 (1992), each of which is hereby incorporated by reference in its entirety). In addition to binding with high affinity to PPARγ, both $PGJ_2$ and 15d-$PGJ_2$ possess an electrophilic α, β-unsaturated carbonyl group in the cyclopentanone ring that reacts covalently with certain nucleophiles in some proteins (Atsmon et al., "Formation of Thiol Conjugates of 9-deoxy-delta 9, delta 12(E)-Prostaglandin D2 and Delta 12(E)-prostaglandin D2," *Biochemistry* 29:3760-3765 (1990); Stamatakis et al., "Identification of Novel Protein Targets for Modification by 15-deoxy-Delta12,14-Prostaglandin J2 in Mesangial Cells Reveals Multiple Interactions with the Cytoskeleton," *J Am Soc Nephrol* 17:89-98 (2006), each of which is hereby incorporated by reference in its entirety). This action accounts for many of the PPARγ-independent activities of J-type prostaglandins, which include the potentiation of apoptosis, reorganization of cytoskeletal proteins, and generation of reactive oxygen species (ROS).

Another class of suitable electrophilic compounds includes, without limitation, pentacyclic tri-terpenoids and tri-terpenoid derivatives of oleanolic and ursolic acids, as well as the tricyclic bis-enones These two groups of compounds are generally denoted by the following structure of formula (I):

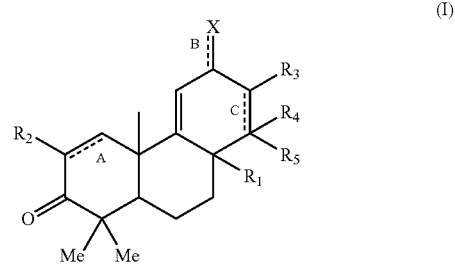

wherein either $R_1$ is cyano or substituted or unsubstituted versions of $C_1$-$C_{15}$-alkyl, $C_2$-$C_{15}$-alkenyl, $C_2$-$C_{15}$-alkynyl, $C_7$-$C_{15}$-aralkyl, $C_2$-$C_{15}$-heteroaralkyl, or $C_1$-$C_{15}$-acyl, and $R_2$, $R_3$, $R_4$, and $R_5$ are each independently hydrogen, hydroxy, amino, cyano, halo, or substituted or unsubstituted versions of $C_1$-$C_{15}$-alkyl, $C_2$-$C_{15}$-alkenyl, $C_2$-$C_{15}$-alkynyl, $C_6$-$C_{15}$-aryl, $C_7$-$C_{15}$-aralkyl, $C_1$-$C_{15}$-heteroaryl, $C_2$-$C_{15}$-heteroaralkyl, $C_1$-$C_{15}$-acyl, $C_1$-$C_{15}$-alkoxy, $C_2$-$C_{15}$-alkenyloxy, $C_2$-$C_{15}$-alkynyloxy, $C_6$-$C_{15}$-aryloxy, $C_7$-$C_{15}$-aralkoxy, $C_1$-$C_{15}$-heteroaryloxy, $C_2$-$C_{15}$-heteroaralkoxy, $C_1$-$C_{15}$-acyloxy, $C_1$-$C_{15}$-alkylamino, $C_2$-$C_{15}$-alkenylamino, $C_2$-$C_{15}$-alkynylamino, $C_6$-$C_{15}$-arylamino, $C_7$-$C_{15}$-aralkylamino, $C_1$-$C_{15}$-heteroarylamino, $C_2$-$C_{15}$-heteroalkylamino, or $C_2$-$C_{15}$-amido; or $R_1$ and $R_4$ are methyl, $R_2$ is hydrogen, hydroxy, amino, cyano, halo, or substituted or unsubstituted versions of $C_1$-$C_{15}$-alkyl, $C_2$-$C_{15}$-alkenyl, $C_2$-$C_{15}$-alkynyl, $C_6$-$C_{15}$-aryl, $C_7$-$C_{15}$-aralkyl, $C_1$-$C_{15}$-heteroaryl, $C_2$-$C_{15}$-heteroaralkyl, $C_1$-$C_{15}$-acyl, $C_1$-$C_{15}$-alkoxy, $C_2$-$C_{15}$-alkenyloxy, $C_2$-$C_{15}$-alkynyloxy, $C_6$-$C_{15}$-aryloxy, $C_7$-$C_{15}$-aralkoxy, $C_1$-$C_{15}$-heteroaryloxy, $C_2$-$C_{15}$-heteroaralkoxy, $C_1$-$C_{15}$-acyloxy, $C_1$-$C_{15}$-alkylamino, $C_2$-$C_{15}$-alkenylamino, $C_2$-$C_{15}$-alkynylamino, $C_6$-$C_{15}$-arylamino, $C_2$-$C_{15}$-aralkylamino, $C_1$-$C_{15}$-heteroarylamino, $C_2$-$C_{15}$-heteroaralkylamino, or $C_2$-$C_{15}$-amido, $R_3$ and $R_5$ are both replaced by a group having the structure (Q) shown below (forming the pentacyclic triterpenoids), with the bond to $R_3$, in the structure above, attached to the carbon atom labeled "3" in the structure below, and, with the bond to $R_5$, in the structure above, attached to the carbon atom labeled "5" in the structure:

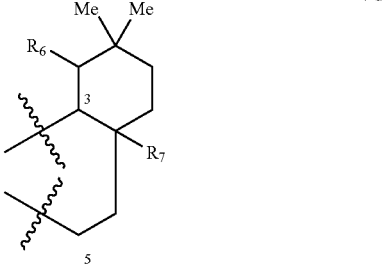

$R_6$ is hydrogen, and $R_7$ is hydrogen, hydroxy, amino, cyano, halo, or substituted or unsubstituted versions of $C_1$-$C_{15}$-alkyl, $C_2$-$C_{15}$-alkenyl, $C_2$-$C_{15}$-alkynyl, $C_7$-$C_{15}$-aralkyl, $C_2$-$C_{15}$-heteroaralkyl, $C_1$-$C_{15}$-acyl, $C_1$-$C_{15}$-alkoxy, $C_2$-$C_{15}$-alkenyloxy, $C_2$-$C_{15}$-alkynyloxy, $C_6$-$C_{15}$-aryloxy, $C_7$-$C_{15}$-aralkoxy, $C_1$-$C_{15}$-heteroaryloxy, $C_2$-$C_{15}$-heteroaralkoxy, $C_1$-$C_{15}$-acyloxy, $C_1$-$C_{15}$-alkylamino, $C_2$-$C_{15}$-alkenylamino, $C_2$-$C_{15}$-alkynylamino, $C_6$-$C_{15}$-arylamino, $C_7$-$C_{15}$-aralkylamino, $C_1C_{15}$-heteroarylamino, $C_2$-$C_{15}$-heteroaralkylamino, or $C_2$-$C_{15}$-amido; further wherein X is selected from the group consisting of -H and =O; A, B, and C each independently signifies a single- or double-bond, provided that (1) when C is a double-bond, $R_4$ is absent, (2) when B is a double bond, X is =O, (3) when B is a single bond, X is —H; any ketone group shown in the above structure may replaced by its enol tautomer, and pharmaceutically acceptable salts, hydrates, and optical isomers thereof. These electrophilic tri-terpenoids and bis-enols are disclosed in PCT Publ. No. WO 2008/064132 to Sporn et al., which is hereby incorporated by reference in its entirety.

According to one embodiment, the triterpenoid is a penta-cyclic triterpenoid according to formula (II):

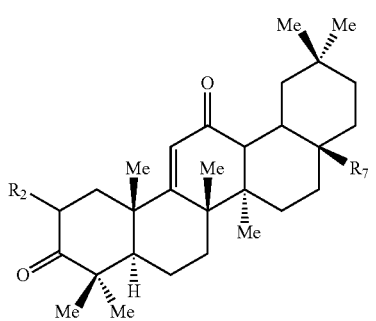

(II)

wherein $R_2$ is hydrogen, hydroxy, amino, cyano, halo, or substituted or unsubstituted versions of $C_1$-$C_{15}$-alkyl, $C_2$-$C_{15}$-alkenyl, $C_2$-$C_{15}$-alkynyl, $C_6C_{15}$-aryl, $C_7$-$C_{15}$-aralkyl, $C_1$-$C_{15}$-heteroaryl, $C_2$-$C_{15}$-heteroaralkyl, $C_1$-$C_{15}$-acyl, $C_1$-$C_{15}$-alkoxy, $C_2$-$C_{15}$-alkenyloxy, $C_2$-$C_{15}$-alkynyloxy, $C_6$-$C_{15}$-aryloxy, $C_7$-$C_{15}$-aralkoxy, $C_1$-$C_{15}$-heteroaryloxy, $C_2$-$C_{15}$-heteroaralkoxy, $C_2$-$C_{15}$-acyloxy, $C_1$-$C_{15}$-alkylamino, $C_2$-$C_{15}$-alkenylamino, $C_2$-$C_{15}$-alkynylamino, $C_6$-$C_{15}$-arylamino, $C_7$-$C_{15}$-aralkylamino, $C_1$-$C_{15}$-heteroarylamino, $C_2$-$C_{15}$-heteroaralkylamino, or $C_2$-$C_{15}$-amido; $R_7$ is hydrogen, hydroxy, amino, cyano, halo, or substituted or unsubstituted versions of $C_1$-$C_{15}$-alkyl, $C_2$-$C_{15}$-alkenyl, $C_2$-$C_{15}$-alkynyl, $C_7$-$C_{15}$-aralkyl, $C_2$-$C_{15}$-heteroaralkyl, $C_7$-$C_{15}$-acyl, $C_1$-$C_{15}$-alkoxy, $C_2$-$C_{15}$-alkenyloxy, $C_2$-$C_{15}$-alkynyloxy, $C_6$-$C_{15}$-aryloxy, $C_7$-$C_{15}$-aralkoxy, $C_1$-$C_{15}$-heteroaryloxy, $C_2$-$C_{15}$-heteroaralkoxy, $C_1$-$C_{15}$-acyloxy, $C_1$-$C_{15}$-alkylamino, $C_2$-$C_{15}$-alkenylamino, $C_2$-$C_{15}$-alkynylamino, $C_6$-$C_{15}$-arylamino, $C_7$-$C_{15}$-aralkylamino, $C_1$-$C_{15}$-heteroarylamino, $C_2$-$C_{15}$-heteroaralkylamino, or $C_2$-$C_{15}$-amido; further wherein any ketone group shown in the above structure may replaced by its enol tautomer, and pharmaceutically acceptable salts, and hydrates thereof. These electrophilic tri-terpenoids are disclosed in PCT Publ. No. WO 2008/064132 to Sporn et al., which is hereby incorporated by reference in its entirety.

In some specific embodiments, the triterpenoid may be defined by formula (III)

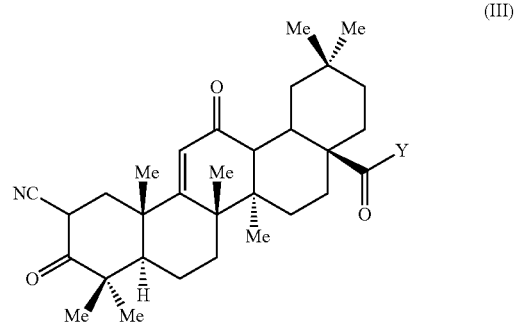

(III)

wherein Y is hydrogen, hydroxy, amino, halo, or a substituted of unsubstituted version of $C_1$-$C_{14}$-alkoxy, $C_2$-$C_{14}$-alkenyloxy, $C_2$-$C_{14}$-alkynyloxy, $C_6$-$C_{14}$-aryloxy, $C_7$-$C_{14}$-aralkoxy, $C_1$-$C_{14}$-heteroaryloxy, $C_2$-$C_{14}$-heteroaralkoxy, $C_1$-$C_{14}$-acyloxy, $C_1$-$C_{14}$-alkylamino, $C_2$-$C_{14}$-alkenylamino, $C_2$-$C_{14}$-alkynylamino, $C_6$-$C_{14}$-arylamino, $C_7$-$C_{14}$-aralkylamino, $C_1$-$C_{14}$-heteroarylamino, $C_2$-$C_{14}$-heteroaralkylamino, $C_1$-$C_{14}$-alkylthio, $C_6$-$C_{14}$-arylthio, $C_7$-$C_{14}$-aralkylthio, $C_1$-$C_{14}$-heteroarylthio, $C_2$-$C_{14}$-heteroaralkylthio, or $C_0$-$C_{14}$-silyl, and substantially free pharmaceutically acceptable salts and hydrates thereof. In certain of these embodiments, Y is hydroxy, methoxy, ethyl-amino, or

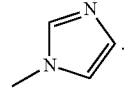

These electrophilic tri-terpenoids are disclosed in PCT Publ. No. WO 2008/064132 to Sporn et al., which is hereby incorporated by reference in its entirety.

In defining the structures in the preceding three paragraphs, PCT Publ. No. WO 2008/064132 to Sporn et al. utilizes the following definitions:

As used herein, the term "amino" means —NH$_2$; the term "nitro" means —NO$_2$; the term "halo" designates —F, —Cl, —Br or —I; the term "mercapto" means —SH; the term "cyano" means —CN; the term "silyl" means —SiH$_3$, and the term "hydroxy" means —OH.

The term "substituted," when used to modify a class of organic radicals (e.g. alkyl, aryl, acyl, etc.), means that one or more than one hydrogen atom of that radical has been replaced by a heteroatom, or a heteroatom containing group. Specific substituted organic radicals are defined more fully below.

The term "unsubstituted," when used to modify a class of organic radicals (e.g. alkyl, aryl, acyl, etc.) means that none of the hydrogen atoms of that radical have been replaced with a heteroatom or a heteroatom containing group. Substitution of a hydrogen atom with a carbon atom, or a group consisting of only carbon and hydrogen atoms, is not sufficient to make a group substituted. Specific unsubstituted organic radicals are defined more fully below.

The term "unsubstituted $C_n$-alkyl" refers to a radical, having a linear or branched, cyclic or acyclic structure, further having no carbon-carbon double or triple bonds, further having a total of n carbon atoms, all of which are nonaromatic, 3 or more hydrogen atoms, and no heteroatoms. For example, an unsubstituted $C_1$-$C_{10}$-alkyl has 1 to 10 carbon atoms. The term "alkyl" includes straight-chain alkyl groups, branchedchain alkyl groups, cycloalkyl (alicyclic) groups, alkyl substituted cycloalkyl groups, and cycloalkyl substituted alkyl groups.

The term "substituted $C_n$-alkyl" refers to a radical, having a single saturated carbon atom as the point of attachment, no carbon-carbon double or triple bonds, further having a linear or branched, cyclic or acyclic structure, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a substituted $C_1C_{10}$-alkyl has 1 to 10 carbon atoms.

The term "unsubstituted $C_n$-alkenyl" refers to a radical, having a linear or branched, cyclic or acyclic structure, further having at least one carbon-carbon double bond, at total of n carbon atoms, all of which are nonaromatic, 3 or more hydrogen atoms, and no heteroatoms. For example, an unsubstituted $C_2$-$C_{10}$-alkenyl has 2 to 10 carbon atoms.

The term "substituted $C_n$alkenyl" refers to a radical, having a single nonaromatic carbon atom as the point of attachment and at least one nonaromatic carbon-carbon double bond, but no carbon-carbon triple bonds, further having a linear or branched, cyclic or acyclic structure, further having a total of n carbon atoms, 0, 1, or more than one hydrogen atom, and at least one heteroatom, wherein each heteroatom is independently selected from the group consisting of N, O, F, Cl, Br, I, Si, P, and S. For example, a substituted $C_2$-$C_{10}$-alkenyl has 2 to 10 carbon atoms.

The term "unsubstituted $C_n$-alkynyl" refers to a radical, having a linear or branched, cyclic or acyclic structure, further having at least one carbon-carbon triple bond, a total of n carbon atoms, all of which are nonaromatic, at least one hydrogen atom, and no heteroatoms. For example, an unsubstituted $C_2$-$C_{10}$-alkynyl has 2 to 10 carbon atoms.

The term "substituted $C_n$-alkynyl" refers to a radical, having a single nonaromatic carbon atom as the point of attachment and at least one nonaromatic carbon-carbon triple bond, further having a linear or branched, cyclic or acyclic structure, and having a total of n carbon atoms, 0, 1, or more than one hydrogen atom, and at least one heteroatom, wherein each heteroatom is independently selected from the group consisting of N, O, F, Cl, Br, I, Si, P, and S. For example, a substituted $C_2$-$C_{10}$-alkynyl has 2 to 10 carbon atoms.

The term "unsubstituted $C_n$-aryl" refers to a radical, having a single carbon atom as a point of attachment, wherein the carbon atom is part of an aromatic ring structure containing only carbon atoms, further having a total of n carbon atoms, 5 or more hydrogen atoms, and no heteroatoms. For example, an unsubstituted $C_6$-$C_{10}$-aryl has 6 to 10 carbon atoms. Aryl groups also include polycyclic fused aromatic groups such as naphthyl, quinolyl, indolyl, and the like.

The term "substituted $C_n$-aryl" refers to a radical, having a single carbon atom as point of attachment, wherein the carbon atom is part of an aromatic ring structure containing only carbon atoms, further having a total of n aromatic or nonaromatic carbon atoms, 0, 1, or more than one hydrogen atom, and at least one nonaromatic heteroatom, wherein each heteroatom is independently selected from the group consisting of N, O, F, Cl, Br, I, Si, P, and S. For example, a substituted $C_6$-$C_{10}$-aryl has 6 to 10 carbon atoms.

The term "unsubstituted $C_n$-aralkyl" refers to a radical, having a single saturated carbon atom as the point of attachment, further having a total of n carbon atoms, wherein at least 6 of the carbon atoms form an aromatic ring structure containing only carbon atoms, 7 or more hydrogen atoms, and no heteroatoms. For example, an unsubstituted $C_7$-$C_{10}$-aralkyl has 7 to 10 carbon atoms. An "aralkyl" includes an alkyl substituted with an aryl group.

The term "substituted $C_n$-aralkyl" refers to a radical, having a single saturated carbon atom as the point of attachment, further having a total of n carbon atoms, wherein at least 6 of the carbon atoms form an aromatic ring structure containing only carbon atoms, 0, 1, or more than one hydrogen atom, and at least one heteroatom, wherein each heteroatom is independently selected from the group consisting of N, O, F, Cl, Br, I, Si, P, and S. For example, a substituted $C_7$-$C_{10}$-aralkyl has 7 to 10carbon atoms.

The term "unsubstituted $C_n$-heteroaryl" refers to a radical, having either a single aromatic carbon atom or a single aromatic heteroatom as the point of attachment, further having a total of n carbon atoms, at least one hydrogen atom, and at least one heteroatom, wherein at least one of the carbon atoms and all of the heteroatoms are incorporated into one or more aromatic ring structures, further wherein each heteroatom is independently selected from the group consisting of N, O, F, Cl, Br, I, Si, P, and S. For example, an unsubstituted $C_1$-$C_{10}$-heteroaryl has 1 to 10 carbon atoms. For example, the term "heteroaryl" includes those groups derived from the compounds: pyrrole, furan, thiophene, imidazole, oxazole, isoxazole, thiazole, isothiazole, triazole, pyrazole, pyridine, pyrazine, pyridazine, pyrimidine, and the like.

The term "substituted $C_n$-heteroaryl" refers to a radical, having either a single aromatic carbon atom or a single aromatic heteroatom as the point of attachment, further having a total of n carbon atoms, at least one hydrogen atom, and at least two heteroatoms, wherein at least one of the carbon atoms and at least one of the heteroatoms are incorporated into one or more aromatic ring structures, further wherein at least one of the heteroatoms is not part of the one or more aromatic ring structures, further wherein each heteroatom is independently selected from the group consisting of N, O, F, Cl, Br, I, Si, P, and S. For example, an substituted $C_1$-$C_{10}$-heteroaryl has 1 to 10 carbon atoms.

The term "unsubstituted $C_n$-heteroaralkyl" refers to a radical, having a single saturated carbon atom as the point of attachment, further having a total of n carbon atoms, at least three hydrogen atoms, and at least one heteroatom, wherein at least one of the carbon atoms and all of the heteroatoms form an aromatic ring structure, further wherein each heteroatom is independently selected from the group consisting of N, O, F, Cl, Br, I, Si, P, and S. For example, an unsubstituted $C_2$-$C_{10}$-heteroaralkyl has 2 to 10 carbon atoms.

The term "substituted $C_n$-heteroaralkyl" refers to a radical having a single saturated carbon atom as the point of attachment, further having a total of n carbon atoms, 0, 1, or more than one hydrogen atom, and at least two heteroatoms, wherein at least one of the carbon atoms and at least one of the heteroatoms are incorporated into one or more aromatic ring structures, further wherein at least one of the heteroatoms is not part of an aromatic ring structure, further wherein each heteroatom is independently selected from the group consisting of N, O, F, Cl, Br, I, Si, P, and S. For example, a substituted $C_2$-$C_{10}$-heteroaralkyl has 2 to 10 carbon atoms.

The term "unsubstituted $C_n$-acyl" refers to a radical, having a single carbon atom of a carbonyl group as the point of attachment, further having a linear or branched, cyclic or acyclic structure, further having a total of n carbon atoms, 1 or more hydrogen atoms, a total of one oxygen atom, and no additional heteroatoms. For example, an unsubstituted $C_1$-$C_{10}$-acyl has 1 to 10 carbon atoms.

The term "substituted $C_n$-acyl" refers to a radical, having a single carbon atom as the point of attachment, the carbon atom being part of a carbonyl group, further having a linear or branched, cyclic or acyclic structure, further having a total of n carbon atoms, 0, 1, or more than one hydrogen atom, at least one additional heteroatom in addition to the oxygen of the carbonyl group, wherein each additional heteroatom is independently selected from the group consisting of N, O, F, Cl, Br, I, Si, P, and S. For example, a substituted $C_1$-$C_{10}$-acyl has 1 to 10 carbon atoms. The term substituted acyl includes carbamoyl, thiocarboxylate, and thiocarboxylic acid groups.

The term "unsubstituted $C_n$-alkoxy" refers to a group, having the structure —OR, in which R is an unsubstituted $C_n$-alkyl, as that term is defined above.

The term "substituted $C_n$-alkoxy" refers to a group, having the structure —OR, in which R is a substituted $C_n$-alkyl, as that term is defined above.

The term "unsubstituted $C_n$-alkenyloxy" refers to a group, having the structure —OR, in which R is an unsubstituted $C_n$-alkenyl, as that term is defined above.

The term "substituted $C_n$-alkenyloxy" refers to a group, having the structure —OR, in which R is a substituted $C_n$-alkenyl, as that term is defined above.

The term "unsubstituted $C_n$-alkynyloxy" refers to a group, having the structure —OR, in which R is an unsubstituted $C_n$-alkynyl, as that term is defined above.

The term "substituted $C_n$-alkenyloxy" refers to a group, having the structure —OR, in which R is a substituted $C_n$-alkynyl, as that term is defined above.

The term "unsubstituted $C_n$aryloxy" refers to a group, having the structure —OAr, in which Ar is an unsubstituted $C_n$aryl, as that term is defined above.

The term "substituted $C_n$-aryloxy" refers to a group, having the structure —OAr, in which Ar is a substituted $C_n$aryl, as that term is defined above.

The term "unsubstituted $C_n$aralkyloxy" refers to a group, having the structure —OAr, in which Ar is an unsubstituted $C_n$aralkyl, as that term is defined above.

The term "substituted $C_n$aralkyloxy" refers to a group, having the structure —OAr, in which Ar is a substituted $C_n$aralkyl, as that term is defined above.

The term "unsubstituted $C_n$-heteroaryloxy" refers to a group, having the structure —OAr, in which Ar is an unsubstituted $C_n$-heteroaryl, as that term is defined above.

The term "substituted $C_n$-heteroaryloxy" refers to a group, having the structure —OAr, in which Ar is a substituted $C_n$-heteroaryl, as that term is defined above.

The term "unsubstituted $C_n$-heteroaralkyloxy" refers to a group, having the structure —OAr, in which Ar is an unsubstituted $C_n$heteroaralkyl, as that term is defined above.

The term "substituted $C_n$heteroaralkyloxy" refers to a group, having the structure —OAr, in which Ar is a substituted $C_n$heteroaralkyl, as that term is defined above.

The term "unsubstituted $C_n$-acyloxy" refers to a group, having the structure —OAc, in which Ac is an unsubstituted $C_n$-acyl, as that term is defined above. An unsubstituted acyloxy group includes alkylcarbonyloxy and arylcarbonyloxy groups.

The term "substituted $C_n$-acyloxy" refers to a group, having the structure —OAc, in which Ac is a substituted $C_n$acyl, as that term is defined above. A substituted acyloxy group includes alkoxycarbonyloxy, aryloxycarbonyloxy, carboxylate, alkylcarbonyl, alkoxycarbonyl, aminocarbonyl, and alkylthiocarbonyl groups.

The term "unsubstituted $C_n$-alkylamino" refers to a radical, having a single nitrogen atom as the point of attachment, further having one or two saturated carbon atoms attached to the nitrogen atom, further having a linear or branched, cyclic or acyclic structure, containing a total of n carbon atoms, all of which are nonaromatic, 4 or more hydrogen atoms, a total of 1 nitrogen atom, and no additional heteroatoms. For example, an unsubstituted $C_1$-$C_{10}$-alkylamino has 1 to 10 carbon atoms. An alkylamino group includes dialkylamino groups.

The term "substituted $C_n$alkylamino" refers to a radical, having a single nitrogen atom as the point of attachment, further having one or two saturated carbon atoms attached to the nitrogen atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a substituted $C_1$-$C_{10}$-alkylamino has 1 to 10 carbon atoms.

The term "unsubstituted $C_n$-alkenylamino" refers to a radical, having a single nitrogen atom as the point of attachment, further having a linear or branched, cyclic or acyclic structure, containing at least one carbon-carbon double bond, a total of n carbon atoms, all of which are nonaromatic, 4 or more hydrogen atoms, a total of one nitrogen atom, and no additional heteroatoms. For example, an unsubstituted $C_2$-$C_{10}$-alkenylamino has 2 to 10 carbon atoms. An alkenylamino group includes dialkenylamino and alkyl(alkenyl)amino groups.

The term "substituted $C_n$-alkenylamino" refers to a radical, having a single nitrogen atom as the point of attachment and at least one nonaromatic carbon-carbon double bond, but no carbon-carbon triple bonds, further having a linear or branched, cyclic or acyclic structure, further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a substituted $C_2$-$C_{10}$-alkenylamino has 2 to 10 carbon atoms.

The term "unsubstituted $C_n$-alkynylamino" refers to a radical, having a single nitrogen atom as the point of attachment, further having a linear or branched, cyclic or acyclic structure, containing at least one carbon-carbon triple bond, a total of n carbon atoms, all of which are nonaromatic, at least one hydrogen atoms, a total of one nitrogen atom, and no additional heteroatoms. For example, an unsubstituted $C_2$-$C_{10}$-alkynylamino has 2 to 10 carbon atoms. An alkynylamino group includes dialkynylamino and alkyl(alkynyl)amino groups.

The term "substituted $C_n$-alkynylamino" refers to a radical, having a single nitrogen atom as the point of attachment, further having at least one nonaromatic carbon-carbon triple bond, further having a linear or branched, cyclic or acyclic structure, and further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a substituted $C_2$-$C_{10}$-alkynylamino has 2 to 10 carbon atoms.

The term "unsubstituted $C_n$-arylamino" refers to a radical, having a single nitrogen atom as the point of attachment, further having at least one aromatic ring structure attached to the nitrogen atom, wherein the aromatic ring structure contains only carbon atoms, further having a total of n carbon atoms, 6 or more hydrogen atoms, a total of one nitrogen atom, and no additional heteroatoms. For example, an unsubstituted $C_6$-$C_{10}$-arylamino has 6 to 10 carbon atoms. An arylamino group includes diarylamino and alkyl(aryl)amino groups.

The term "substituted $C_n$-arylamino" refers to a radical, having a single nitrogen atom as the point of attachment, further having at least one aromatic ring structure attached to the nitrogen atom, wherein the aromatic ring structure contains only carbon atoms, further having a total of n carbon atoms, 0, 1, or more hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a substituted $C_6$-$C_{10}$-arylamino has 6 to 10 carbon atoms.

The term "unsubstituted $C_n$-aralkylamino" refers to a radical, having a single nitrogen atom as the point of attachment, further having one or two saturated carbon atoms attached to the nitrogen atom, further having a total of n carbon atoms, wherein at least 6 of the carbon atoms form an aromatic ring structure containing only carbon atoms, 8 or more hydrogen atoms, a total of one nitrogen atom, and no additional heteroatoms. For example, an unsubstituted $C_7$-$C_{10}$-aralkylamino has 7 to 10 carbon atoms. An aralkylamino group includes diaralkylamino, alkyl(aralkyl)amino, and aryl(aralkyl)amino groups.

The term "substituted $C_n$-aralkylamino" refers to a radical, having a single nitrogen atom as the point of attachment, further having at least one or two saturated carbon atoms attached to the nitrogen atom, further having a total of n carbon atoms, wherein at least 6 of the carbon atoms form an aromatic ring structure containing only carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a substituted $C_7$-$C_{10}$-aralkylamino has 7 to 10 carbon atoms.

The term "unsubstituted $C_n$-heteroarylamino" refers to a radical, having a single nitrogen atom as the point of attachment, further having a total of n carbon atoms, at least one hydrogen atom, and at least one additional heteroatom, in addition to the nitrogen atom at the point of attachment, wherein at least one of the carbon atoms and all of the additional heteroatoms are incorporated into one or more aromatic ring structures, further wherein each additional heteroatom is independently selected from the group consisting of N, O, F, Cl, Br, I, Si, P, and S. For example, an unsubstituted $C_1$-$C_{10}$-heteroarylamino has 1 to 10 carbon atoms. A heteroaryl amino group includes alkyl(heteroaryl)amino and aryl(heteroaryl)amino groups.

The term "substituted C-heteroarylamino" refers to a radical, having a single nitrogen atom as the point of attachment, further having a total of n carbon atoms, at least one hydrogen atom, at least two additional heteroatoms, that is, in addition to the nitrogen atom at the point of attachment, wherein at least one of the carbon atoms and at least one of the additional heteroatoms are incorporated into one or more aromatic ring structures, further wherein at least one of the additional heteroatoms is not part of the one or more aromatic ring structures, further wherein each additional heteroatom is independently selected from the group consisting of N, O, F, Cl, Br, I, Si, P, and S. For example, an substituted $C_1$-$C_{10}$-heteroarylamino has 1 to 10 carbon atoms.

The term "unsubstituted $C_n$-heteroaralkylamino" refers to a radical, having a single nitrogen atom as the point of attachment, further having one or two saturated carbon atoms attached to the nitrogen atom, further having a total of n carbon atoms, at least three hydrogen atoms, at least one additional heteroatom, wherein at least one of the carbon atoms and all of the additional heteroatoms form an aromatic ring structure, further wherein each additional heteroatom is independently selected from the group consisting of N, O, F, Cl, Br, I, Si, P, and S. For example, an unsubstituted $C_2$-$C_{10}$-heteroaralkylamino has 2 to 10 carbon atoms. A heteroaralkylamino group includes alkyl(heteroaralkyl)amino and aryl(heteroaralkyl)amino groups.

The term "substituted C-heteroaralkylamino" refers to a radical, having a single nitrogen atom as the point of attachment, further having one or two saturated carbon atoms attached to the nitrogen atom, further having a total of n carbon atoms, 0, 1, or more than one hydrogen atom, at least two additional heteroatoms, that is, in addition to the nitrogen atom at the point of attachment, wherein at least one of the carbon atoms and at least one of the additional heteroatoms are incorporated into one or more aromatic ring structures, further wherein at least one of the heteroatoms is not part of an aromatic ring structure, further wherein each heteroatom is independently selected from the group consisting of N, O, F, Cl, Br, I, Si, P, and S. For example, a substituted $C_2$-$C_{10}$-heteroaralkylamino has 2 to 10 carbon atoms.

The term "unsubstituted $C_n$-amido" refers to a radical, having a single nitrogen atom as the point of attachment, further having a carbonyl group attached via its carbon atom to the nitrogen atom, further having a linear or branched, cyclic or acyclic structure, further having a total of n carbon atoms, 1 or more hydrogen atoms, a total of one oxygen atom, a total of one nitrogen atom, and no additional heteroatoms. For example, an unsubstituted $C_1$-$C_{10}$-amido has 1 to 10 carbon atoms. A amido group includes N-alkyl-amido, N-aryl-amido, N-aralkyl-amido, acylamino, al kylcarbonylamino, arylcarbonylamino, and ureido groups.

The term "substituted $C_n$-amido" refers to a radical, having a single nitrogen atom as the point of attachment, further having a carbonyl group attached via its carbon atom to the nitrogen atom, further having a linear or branched, cyclic or acyclic structure, further having a total of n aromatic or non-aromatic carbon atoms, 0, 1, or more than one hydrogen atom, at least one additional heteroatom in addition to the oxygen of the carbonyl group, wherein each additional heteroatom is independently selected from the group consisting of N, O, F, Cl, Br, I, Si, P, and S. For example, a substituted $C_1$-$C_{10}$-amido has 1 to 10 carbon atoms.

A number of these tri-terpenoid derivatives of oleanic and urolic acid are described in Dinkova-Kostova et al., "Extremely Potent Triterpenoid Inducers of the Phase 2 Response: Correlations of Protection Against Oxidant and Inflammatory Stress," *Proc Natl Acad Sci USA* 102(12):4584-4589 (2005); Honda et al., "Design and Synthesis of 2-Cyano-3,12-Dioxoolean-1,9-Dien-28-Oic Acid, A Novel and Highly Active Inhibitor of Nitric Oxide Production in Mouse Macrophages," *Bioorg Med Chem Lett* 8:2711-2714 (1998); Honda et al., "Novel Synthetic Oleane and Ursane Triterpenoids with Various Enone Functionalities in Ring A as Inhibitors of Nitric Oxide Production in Mouse Macrophages," *J Med Chem* 43:1866-1877 (2000); Honda et al., "Synthetic Oleane and Ursane Triterpenoids with Modified Rings A and C: A Series of Highly Active Inhibitors of Nitric Oxide Production in Mouse Macrophages," *J Med Chem* 43:4233-4246 (2000); Honda et al., "A Novel Dicyanotriterpenoid, 2-Cyano-3,12-Dioxooleana-1,9(11)-Dien-28-Onitrile, Active at Picomolar Concentrations for Inhibition of Nitric Oxide Production," *Bioorg Med Chem Lett* 12:1027-1030 (2002); Place et al., "The Novel Synthetic Triterpenoid, CDDO-Imidazole, Inhibits Inflammatory Response and Tumor Growth in Vivo,"

*Clin Cancer Res.* 9:2798-2806 (2003), each of which is hereby incorporated by reference in its entirety.

Exemplary tri-terpenoid derivatives of oleanic acid include, without limitation, 2-cyano-3,12-dioxoolean-1,9-dien-28-oic acid (CDDO) and the CDDO-derivatives 2-cyano-3,12-dioxooleana-1,9-dien-28-oic imidazolide (CDDO-Im), the methyl ester of CDDO (CDDO-Me), the ethylamide of CDDO, and the cyano derivative of CDDO, and the various derivatives of CDDO described in U.S. Patent Application Publ. Nos. 2004/0002463 to Honda et al., 2002/0042535 to Gribble et al., and 2005/0288363 to Gribble et al., each of which is hereby incorporated by reference in its entirety. Specific derivatives of CDDO described in U.S. Patent Application Publ. No. 2004/0002463 to Honda et al. include compounds of formula (II) where $R_2$ is —CN and $R_7$ is —CN, as well as compounds of formula (III) where Y is —NH$_2$; —NHNH$_2$;

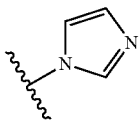 [SMILES: *n1ccnc1]

(unsubstituted imidazole group);

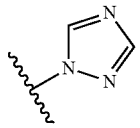 [SMILES: *n1cncn1]

(unsubstituted triazole group);

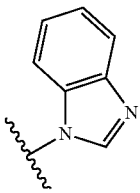 [SMILES: *n1cnc2ccccc21]

(unsubstituted benzimidazole group); the following substituted imidazole groups:

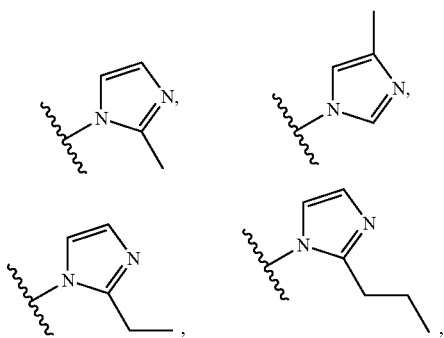

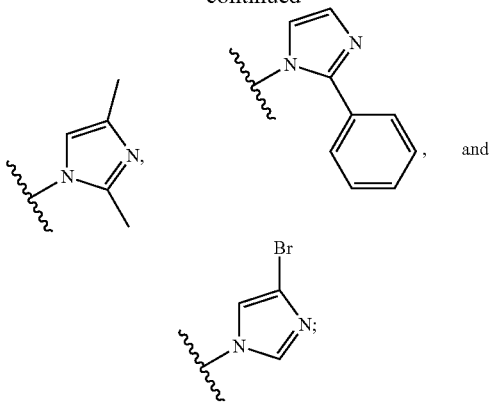

and the following glycosides -D-Glu(OMe)$_4$, -D-Glu(OAc)$_4$, -L-Ara(OAc)$_3$, and -D-Gal-(OAc)$_4$. Additional electrophilic tri-terpenoids are disclosed in PCT Publ. No. WO 2008/064132 to Sporn et al., which is hereby incorporated by reference in its entirety.

Tri-cyclic bis-enone derivatives of formula (I), where $R_3$ and $R_5$ are not collectively the structure (O), are also described in U.S. Patent Application Publ. No. 2003/0232786 to Honda et al., which is hereby incorporated by reference in its entirety. Additional electrophilic tri-cyclic bis-enone derivatives are disclosed in PCT Publ. No. WO 2008/064132 to Sporn et al., which is hereby incorporated by reference in its entirety.

Exemplary tri-cyclic bis-enones include, without limitation, (4bS,8aR,10aR)-3,4b,7,8,8a,9,10,10a-octahydro-4b,8,8-trimethyl-3,7-dioxo-10a-(prop-1-ynyl)phenanthrene-2,6-dicarbonitrile; (4bS,8aR,10aR)-10a-(but-1-ynyl)-3,4b,7,8,8a,9,10,10a-octahydro-4b,8,8-trimethyl-3,7-dioxophenanthrene-2,6-dicarbonitrile; (4bS,8aR,10aR)-10a-(buta-1,3-diynyl)-3,4b,7,8,8a,9,10,10a-octahydro-4b,8,8-trimethyl-3,7-dioxophenanthrene-2,6-dicarbonitrile; (4bS,8aR,10aR)-3,4b,7,8,8a,9,10,10a-octahydro-10a-(3-hydroxyprop-1-ynyl)-4b,8,8-trimethyl-3,7-dioxophenanthrene-2,6-dicarbonitrile; (4bS,8aR,10aR)-3,4b,7,8,8a,9,10,10a-octahydro-10a-(3-alkoxyprop-1-ynyl)-4b,8,8-trimethyl-3,7-dioxophenanthrene-2,6-dicarbonitrile, where the alkoxy is methyl or ethyl; (4bS,8aR,10aR)-10a-(2-haloethynyl)-3,4b,7,8,8a,9,10,10a-octahydro-4b,8,8-trimethyl-3,7-dioxophenanthrene-2,6-dicarbonitrile, where the halo is bromo, chloro, or fluoro; (4bS,8aR,10aR)-10a-(2-cyanoethynyl)-3,4b,7,8,8a,9,10,10a-octahydro-4b,8,8-trimethyl-3,7-dioxophenanthrene-2,6-dicarbonitrile; (4bS,8aR,10aR)-10a-(4-aminobut-1-ynyl)-3,4b,7,8,8a,9,10,10a-octahydro-4b,8,8-trimethyl-3,7-dioxophenanthrene-2,6-dicarbonitrile and its hydrochloride salt; 3-((4aS,8aR,10aR)-3,7-dicyano-1,2,4a,6,8a,9,10,10a-octahydro-1,1,4a-trimethyl-2,6-dioxophenanthren-8a-yl)propiolic acid; alkyl 3-((4aS,8aR,10aR)-3,7-dicyano-1,2,4a,6,8a,9,10,10a-octahydro-1,1,4a-trimethyl-2,6-dioxophenanthren-8a-yl)propiolate, where the alkyl ester is methyl, ethyl, or propyl; 3-((4aS,8aR,10aR)-3,7-dicyano-1,2,4a,6,8a,9,10,10a-octahydro-1,1,4a-trimethyl-2,6-dioxophenanthren-8a-yl)propiolamide; 3-((4aS,8aR,10aR)-3,7-dicyano-1,2,4a,6,8a,9,10,10a-octahydro-1,1,4a-trimethyl-2,6-dioxophenanthren-8a-yl)-N-alkylpropiolamide, where the alkyl is methyl, ethyl, or 2,2,2-trifluoroethyl; (4bS,8aR,10aR)-3,4b,7,8,8a,9,10,10a-octahydro-4b,8,8-trimethyl-3,7-dioxo-10a-(3-oxobut-1-ynyl)phenanthrene-2,6-dicarbonitrile; (4bS,8aR,10aR)-10a-(2-formylethynyl)-3,4b,7,8,8a,9,10,10a-octahydro-4b,8,8- trimethyl-3,7-dioxophenanthrene-2,6-dicarbonitrile; (4bS, 8aR,10aR)-3,4b,7,8,8a,9,10,10a-octahydro-10a-(3-methoxyprop-1-ynyl)-4b,8,8-trimethyl-3,7-dioxophenanthrene-2,6-dicarbonitrile; and (4bS,8aR,10aR)-3,4b,7,8,8a,9,10,10a-octahydro-4b,8,8-trimethyl-3,7-dioxo-10a-(3-phenoxyprop-1-ynyl)phenanthrene-2,6-dicarbonitrile.

Another class of suitable electrophilic compounds includes, without limitation, pentacyclic electrophilic tri-terpenoid derivatives of betulin and betulinic acids. These are generally denoted by the following structure of formula (IV):

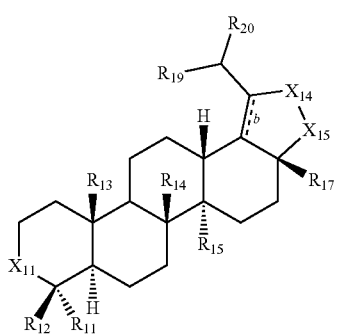

(IV)

wherein $X^{11}$ is C=O, C=NOR$^{11a}$, CHOR$^{11a}$, CHOCOR$^{11a}$, CHOC(O)OR$^{21}$, CHOC(O)OR$^{11a}$, CHOC(O)OR$^{22}$, or CHOCOY-Hal; $X^{14}$ is CH$_2$, CH-Hal, C=O, CHOR$^{11b}$, CHOCOR$^{11b}$, or CHOC(O)OR$^{21}$; $X^{15}$ is CH$_2$, CH-Hal, C=O, CHOR$^{11b}$, CHOCOR$^{11b}$, or CHOC(O)OR$^{21}$; $R^{11-15}$ are H or lower alkyl; $R^{17}$ is COOR$^{11c}$, COOR$^{22}$, CO-Hal, C(O)OC(O)R$^{11c}$, COOYOCOR$^{11c}$, CH$_2$OR$^{11c}$, CH$_2$OCOR$^{11c}$, or CH$_2$OC(O)OR$^{21}$; $R^{19}$ is R$^{11d}$, OR$^{11d}$, CH$_2$-Hal, CH$_2$OR$^{11d}$, CH$_2$OC(O)OR$^{21}$, or =CHR$^{11d}$; $R^{20}$ is R$^{11e}$, CH=NOR$^{11e}$, CN, COOR$^{11e}$, COR$^{11e}$, CH$_2$-Hal, CH$_2$OR$^{11e}$, CH$_2$OCOR$^{11e}$, CH$_2$OC(O)OR$^{21}$, CH$_2$OSO$_2$CH$_3$, or CH$_2$OSO$_2$C$_6$H$_4$CH$_3$; $R^{21}$ is an OH-substituted alkyl group, an ether group or a cyclic ether; $R^{22}$ is lower alkyl substituted by Hal; "b" is a double bond or a single bond; Y=(CH$_2$)$_n$ with n being 0 to 5; $R^{11a-11e}$ are the same or different groups of $R^{11}$; and Hal is Cl, Br, I, or F. This class of tri-terpenoids is described in U.S. Patent Application Publ. Nos. 2004/0087560 to Hajduch et al., 2004/0266868 to Hajduch et al., and 2006/0160890 to Hajduch et al., each of which is hereby incorporated by reference in its entirety.

Exemplary tri-terpenoid derivatives of betulin and betulinic acid include, without limitation, (3aS,5aR,5bR,9S,11aR)-methyl 9-acetoxy-3,3a,4,5,5a,5b,6,7,7a,8,9,10,11,11a,11b,12,13,13a-octadecahydro-1-isopropyl-5a,5b,8,8,11a-pentamethyl-2,3-dioxo-2H-cyclopenta[a]chrysene-3a-carboxylate; (3aS,5aR,5bR,9S,11aR)-methyl 3,3a,4,5,5a,5b,6,7,7a,8,9,10,11,11a,11b,12,13,13a-octadecahydro-9-hydroxy-1-isopropyl-5a,5b,8,8,11a-pentamethyl-2,3-dioxo-2H-cyclopenta[a]chrysene-3a-carboxylate; and (1R,3aS,5aR,5bR,9S,11aR)-1-(1-formylvinyl)-icosahydro-9-hydroxy-5a,5b,8,8,11a-pentamethyl-1H-cyclopenta[a]chrysene-3a-carboxylic acid. Additional electrophilic tri-terpenoids are disclosed in U.S. Patent Application Publ. Nos. 2004/0087560 to Hajduch et al., 2004/0266868 to Hajduch et al., and 2006/0160890 to Hajduch et al., each of which is hereby incorporated by reference in its entirety.

The synthesis of these triterpenoid compounds is described in the patent publications listed in the preceding paragraphs as well as in Dinkova-Kostova et al., "Extremely Potent Triterpenoid Inducers of the Phase 2 Response: Correlations of Protection Against Oxidant and Inflammatory Stress," *Proc Natl Acad Sci USA* 102(12):4584-4589 (2005); Honda et al., "Design and Synthesis of 2-Cyano-3,12-Dioxoolean-1,9-Dien-28-Oic Acid, A Novel and Highly Active Inhibitor of Nitric Oxide Production in Mouse Macrophages," *Bioorg Med Chem Lett* 8:2711-2714 (1998); Honda et al., "Novel Synthetic Oleane and Ursane Triterpenoids with Various Enone Functionalities in Ring A as Inhibitors of Nitric Oxide Production in Mouse Macrophages," *J Med Chem* 43:1866-1877 (2000); Honda et al., "Synthetic Oleane and Ursane Triterpenoids with Modified Rings A and C: A Series of Highly Active Inhibitors of Nitric Oxide Production in Mouse Macrophages," *J Med Chem* 43:4233-4246 (2000); Honda et al., "A Novel Dicyanotriterpenoid, 2-Cyano-3,12-Dioxooleana-1,9(11)-Dien-28-Onitrile, Active at Picomolar Concentrations for Inhibition of Nitric Oxide Production," *Bioorg Med Chem Lett* 12:1027-1030 (2002); Place et al., "The Novel Synthetic Triterpenoid, CDDO-Imidazole, Inhibits Inflammatory Response and Tumor Growth in Vivo," *Clin Cancer Res.* 9:2798-2806 (2003), each of which is hereby incorporated by reference in its entirety.

Also contemplated is the use of any combination of the above-identified electrophilic compounds, particularly among the different classes of electrophilic compounds, e.g., a prostaglandin or prostaglandin derivative in combination with a tri-terpenoid, a prostaglandin or prostaglandin derivative in combination with a tri-cyclic bis-enone derivative, a tri-terpenoid in combination with a tri-cyclic bis-enone derivative, or a combination of a prostaglandin or prostaglandin derivative, a tri-terpenoid, and a tri-cyclic bis-enone derivative.

Suitable salts and prodrugs of the above classes of compounds can also be administered. A number of salts and prodrugs are described in U.S. Patent Application Publ. Nos. 2004/0002463 to Honda et al., 2002/0042535 to Gribble et al., and 2005/0288363 to Gribble et al., 2004/0087560 to Hajduch et al., 2004/0266868 to Hajduch et al., 2006/0160890 to Hajduch et al., and 2003/0232786 to Honda et al., and PCT Publ. No. WO 2008/064132 to Sporn et al. each of which is hereby incorporated by reference in its entirety.

Although the electrophilic compound(s) can be administered to the patient or used for ex vivo purposes alone, the compound(s) will generally be administered in admixture with a pharmaceutical carrier, excipient or diluent selected with regard to the intended route of administration and standard pharmaceutical practice.

Thus, the present invention also relates to pharmaceutical compositions that include the electrophilic compound(s) or pharmaceutically acceptable prodrugs, salts or esters thereof, together with at least one pharmaceutically acceptable excipient, diluent or carrier.

By way of example, in the pharmaceutical compositions of the present invention, the compounds of the invention may be admixed with any suitable binders, lubricants, suspending agents, coating agents, and/or solubilizing agents. Examples of such suitable excipients for the various different forms of pharmaceutical compositions described herein may be found in the *Handbook of Pharmaceutical Excipients*, 2d Edition, (1994), Edited by A Wade and P J Weller, which is hereby incorporated by reference in its entirety.

The pharmaceutical compositions of the present invention may be adapted for administration orally, rectally, vaginally, parenterally, intramuscularly, intraperitoneally, intraarterially, intrathecally, intrabronchially, subcutaneously, intradermally or transdermally, intravenously, or via nasal, buccal or sublingual routes. Of these, intravenous or intraarterial routes are preferred.

For oral administration, particular use is made of compressed tablets, pills, tablets, gels, drops, and capsules. Compositions may be formulated in unit dosage form, i.e., in the form of discrete portions containing a unit dose, or a multiple or sub-unit of a unit dose. Preferably, these compositions contain from 1 to 250 mg and more preferably from 10-100 mg, of active ingredient per dose; however, any effective dose is contemplated herein.

Other forms of administration comprise solutions or emulsions which may be injected intravenously, intraarterially, intrathecally, subcutaneously, intradermally, intraperitoneally or intramuscularly, and which are prepared from sterile or sterilizable solutions. Injectable forms may contain between 1-1000 mg, preferably between 5-500 mg, of active ingredient per dose; however, any effective dose is contemplated herein.

The pharmaceutical compositions of the present invention may also be in form of suppositories, suspensions, emulsions, lotions, ointments, creams, gels, sprays, solutions or dusting powders.

An alternative means of transdermal administration is by use of a skin patch. For example, the active ingredient can be incorporated into a cream that includes an aqueous emulsion of polyethylene glycols or liquid paraffin. The active ingredient can also be incorporated, at a concentration of between 1 and 10% by weight, into an ointment including a white wax or white soft paraffin base together with such stabilizers and preservatives as may be required.

In addition to the above-described formulations which are intended to immediately deliver the active agents to the patient, sustained release formulations are also contemplated. Preferably, the sustained release formulation is an implantable device that includes a matrix in which the electrophilic compound is captured. Other active agents, such as those described below, may also be included for sustained release. Release of the agents can be controlled via selection of materials and the amount of drug loaded into the vehicle. A number of suitable implantable delivery systems are known in the art, such as U.S. Pat. No. 6,464,687 to Ishikawa et al., U.S. Pat. No. 6,074,673 to Guillen, each of which is hereby incorporated by reference in its entirety.

Implantable, sustained release drug delivery systems can be formulated using any suitable biocompatible matrix into which an agent can be loaded for sustained-release delivery. These include, without limitation, microspheres, hydrogels, polymeric reservoirs, cholesterol matrixes, polymeric systems and non-polymeric systems, etc. Exemplary polymeric matrixes include, without limitation, poly(ethylene-co-vinyl acetate), poly-L-lactide, poly-D-lactide, polyglycolide, poly (lactide-co-glycolide), polyanhydride, polyorthoester, polycaprolactone, polyphospagene, proteinaceous polymer, polyether, silicone, and combinations thereof.

A person of ordinary skill in the art can easily determine an appropriate dose of one of the instant compositions to administer to a subject without undue experimentation. Typically, a physician will determine the actual dosage which will be most suitable for an individual patient and it will vary with the age, weight and response of the particular patient The dosages disclosed herein are exemplary. There can of course be individual instances where higher or lower dosage ranges are merited, and such are within the scope of this invention. In an exemplary embodiment, one or more doses of 5 to 150 mg/day will be administered to the patient for the treatment of thrombocytopenia.

The present invention also relates to therapeutic systems and pharmaceutical compositions that include, in addition to one or more of the electrophilic compounds, an agent that increases megakaryocyte production.

Exemplary agents that increase megakaryocyte production include, without limitation, thrombopoietin (TPO), TPO peptide fragments (Takedatsu et al., "Determination of Thrombopoietin-Derived Peptides Recognized by Both Cellular and Humoral Immunities in Healthy Donors and Patients with Thrombocytopenia," Stem Cells 23(7):975-982 (2005); combinations of granulocyte colony stimulating factor (G-CSF) with either interleukin-3 or granulocyte-macrophage colony stimulating factor (GM-CSF), and optionally a pharmaceutically effective amount of interleukin-6 (U.S. Pat. No. 5,762, 920 to Yung et al., which is hereby incorporated by reference in its entirety); a combination of GM-CSF and interleukin-5 (U.S. Pat. No. 5,762,920 to Yung et al., which is hereby incorporated by reference in its entirety); Kuter, "New Thrombopoietic Growth Factors," Blood 109(11):4607-4616 (2007), each of which is hereby incorporated by reference in its entirety), megakaryocyte growth and development factor (MGDF), pegylated recombinant human megakaryocyte growth and development factor (PEG-rHuMGDF) (Kuter et al., "Thrombopoietin Therapy Increases Platelet Yields in Healthy Platelet Donors," Blood 98:1339-45 (2001), which is hereby incorporated by reference in its entirety), small molecule c-Mpl activators such as NIP-004 (structure below) (Nakamura et al., "A Novel Non-peptidyl Human c-Mpl Activator Stimulates Human Megakaryopoiesis and Thrombopoiesis," Blood 107:4300-7 (2006), which is hereby incorporated by reference in its entirety), and ITP-suitable peptibody (Amgen AMG 531).

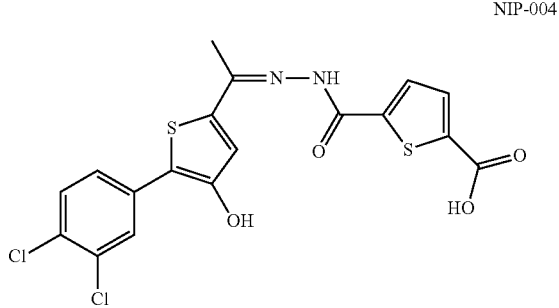 [SMILES: CC(=NNC(=O)c1ccc(C(=O)O)s1)c1cc(O)c(-c2ccc(Cl)c(Cl)c2)s1]

NIP-004

Co-administration can be achieved simultaneously (either in a single formulation or delivery vehicle) or by administering the electrophilic compound and administering the agent that increases megakaryocyte production at the same time (albeit at different sites); or by administering the electrophilic compound and administering the agent that increases megakaryocyte production at different times. In the latter embodiment, it is desirable in some instances to first administer the agent that increases megakaryocyte production (to stimulate megakaryocyte production), followed by administering the electrophilic compound after a suitable time delay. This helps to ensure adequate numbers of megakaryocytes to induce subsequent platelet production caused by administration of the electrophilic compound.

For ex vivo usage, the megakaryocytes can be harvested and maintained in a suitable cell culture environment. For example, three-dimensional cell cultures that replicate the bone marrow environment (Panoskaltsis et al., "Engineering a Mimicry of Bone Marrow Tissue ex vivo," J Biosci Bioeng.

100(1):28-35 (2005), which is hereby incorporated by reference in its entirety) can be used to maintain megakaryocytes and allow for the harvesting of generated platelets. Harvested platelets can be packaged and administered to patients in a manner similar to that of conventional platelet therapies. Because these conditions can be controlled, and a patient's own bone marrow harvested for this purpose, there is reduced risk of transmitting an infectious agent to a patient during platelet administration.

As a consequence of administering the pharmaceutical compositions or therapeutic systems of the present invention, it is also contemplated that that platelet product induced thereby has an effectively increased circulating half-life, thereby sustaining the platelet count and minimizing the frequency of intervention, as well as an improved quality (or activity). This includes the quality of those platelets produced as a result of the administered electrophilic compound as well as existing platelets that remain in circulation following administration of the electrophilic compound. Normally, platelets that are produced from damaged (ionizing radiation) and/or defective megakaryocytes can cause unwanted blood clotting. Use of the electrophilic compounds should have cytoprotective efforts on the megakaryocytes, thereby leading to the production of normal, rather than defective or partially activated platelets.

EXAMPLES

The following examples are provided to illustrate embodiments of the present invention but are by no means intended to limit its scope.

Materials and Methods for Examples 1-10

Reagents and Antibodies 15-deoxy-$\Delta^{12,14}$-PGJ$_2$ (15d-PGJ$_2$) and rosiglitazone were purchased from Biomol (Plymouth Meeting, Pa.); 15-deoxy-$\Delta^{12,14}$-PG2$_2$ (15d-PGD$_2$), PGJ$_2$, 9, dihydro-15d-PGJ$_2$ (CAY10410), PGE$_2$, PGI$_2$, PGF$_{2\alpha}$, and GW9662 were purchased from Cayman Chemical (Ann Arbor, Mich.); N-acetylcysteine (NAC), glutathione reduced ethyl ester (GSH-EE), and fibrinogen were all purchased from Sigma (St. Louis, Mo.); 2-cyano-3,12-dioxoolean-1,9-dien-28-oic acid (CDDO) was obtained from the NIH-RAID program, as well as from Reata Inc. (Texas); C-28 methyl ester of CDDO (CDDO-Me) was a gift from Dr. Michael Sporn (Dartmouth College, Hanover, N.H.); 5-(and-6-)-carboxy-2',7'-dicholorodihydrofluorescein diacetate (carboxy-H$_2$DCFDA) and MitoSOX Red were purchased from Invitrogen (Carlsbad, Calif.); collagen from Chrono-log Corporation (Havertown, Pa.); CD61-FITC (GPIIIa), CD41-FITC (GPIIb), CD61-PE, and annexin V-FITC were purchased from BD Biosciences (San Jose, Calif.); GPIbβ and GPV were purchased from Emfret Analytics (Wurtzburg, Germany); recombinant human thrombopoietin (rhTPO) was purchased from R&D Systems (Minneapolis, Minn.); BIT9500 was purchased from (StemCell Technologies, Vancouver, Canada); total actin (CP-01) was from Oncogene (Cambridge, Mass.).

Cell Line Culture and Treatment Conditions

Meg-01 and M07e cells were purchased from the American Type Culture Collection (Rockville, Md.) and Dami cells were a generous gift from Dr. Patricia J. Simpson-Haidaris (University of Rochester). All cells were cultured in RPMI-1640 tissue culture medium (Invitrogen) supplemented with 5% fetal bovine serum (FBS; Invitrogen), 10 mM HEPES (N-2-hydroxyethylpiperazine-N'-2-ethanesulfonic acid; Sigma), 2 mM L-glutamine (Invitrogen), 4.5 g/L glucose (Invitrogen), and 50 μg/mL gentamicin (Invitrogen). M07e cells were also supplemented with 100 ng/mL of granulocyte monocyte-colony stimulating factor (GM-CSF, R&D Systems). All treatments were performed in normal growth media. Dimethyl sulfoxide (DMSO) was used as a vehicle (control) in the experiments described below.

Megakaryocyte Differentiation from Mouse Bone Marrow

Bone marrow was isolated from the femora of male C57BL/6 mice (Jackson Laboratories, Bar Harbor, Me.) and plated at a concentration of $1\times10^6$ cells per well in 12-well plates in IMDM (Iscove's Modified Dulbecco's Media, Invitrogen) with 20% BIT 9500 (BSA, insulin, transferrin) and supplemented with 100 ng/mL of rhTPO. Cells were cultured for 5 days, following which 15d-PGJ$_2$ (10 μM) was added to the culture medium for 24 h. On the sixth day, cells were examined by phase-contrast microscopy using an inverted microscope (Olympus IX81) and images were captured using SPOT RT software (New Hyde Park, N.Y.). Megakaryocytes were identified by preincubating with anti-mouse CD16/32 (FcγR-blocking antibody) and then incubating with PE-conjugated hamster anti-mouse CD41 antibody.

Megakaryocyte Differentiation from Human Cord Blood-Derived CD34+ Cells

Human CD34+ cord blood cells were obtained from the National Disease Research Interchange (NDRI, Philadelphia, Pa.). Cells were plated at $2.5\times10^5$ cells per well in a 12-well plate and cultured in serum-free medium as previously described (Zeuner et al., "Chemotherapy-induced Thrombocytopenia Derives from the Selective Death of Megakaryocyte Progenitors and Can Be Rescued by Stem Cell Factor," *Cancer Res* 67:4767-4773 (2007), which is hereby incorporated by reference in its entirety) and supplemented with 100 ng/mL of rhTPO. After 14 days in culture, megakaryocytes were identified by staining with a CD61-FITC antibody and analyzed on a BD Biosciences FACSCalibur flow cytometer. Data were analyzed using FlowJo software (Treestar, Ashland, Oreg.). Cell images were captured using an inverted microscope (Olympus IX81).

Platelet Isolation and Platelet Production Analysis

Platelets were isolated from megakaryocytes by centrifugation at 150 xg for 10 min. Supernatants underwent sequential centrifugation (500 xg for 10 min and 1000xg for 10 min). The remaining platelet pellet was fixed then permeabilized with a CD61 or CD41 antibody. 7-AAD (BD Pharmingen) was added for 10 min before analyzing the cells by flow cytometry. Platelets were identified using three well-described parameters (Patel et al., "The Biogenesis of Platelets from Megakaryocyte Proplatelets," *J Clin Invest* 115:3348-3354 (2005); Breton-Gorius et al., "Expression of Platelet Proteins During the In Vitro and In Vivo Differentiation of Megakaryocytes and Morphological Aspects of Their Maturation," *Semin Hematol* 23:43-67 (1986); Ogura et al., "Establishment of a Novel Human Megakaryoblastic Leukemia Cell Line, MEG-01, With Positive Philadelphia Chromosome," *Blood* 66:1384-1392 (1985) and Franks et al., "A Fluorescence Microscopy Method for Quantifying Levels of Prostaglandin Endoperoxide H Synthase-1 and CD-41 in MEG-01 Cells," *Biol Proced Online* 3:54-63 (2001), each of which is hereby incorporated by reference in its entirety), size (using normal human platelets as a control), presence of CD61 or CD41 and lack of DNA as determined by the absence of 7-AAD staining Ten thousand platelet events were collected and platelets were quantified by rate (platelet events/second) (Chung et al., "Platelet Activation in Acute, Decompensated Congestive Heart Failure," *Thromb Res* 120: 709-713 (2007), which is hereby incorporated by reference in its entirety.

Human Blood Platelet Isolation

Whole blood was obtained, with appropriate donor and institutional approvals, from male and female donors by venipuncture into a citrate phosphate dextrose adenine solution containing collection bag (Baxter Fenwal, Round Lake, Ill.) or Vacutainer tubes containing buffered citrate sodium (BD Biosciences, Franklin Lakes, N.J.). Platelets were then isolated according to known procedures (Akbiyik et al., "Human Bone Marrow Megakaryocytes and Platelets Express PPARγ, and PPARγ Agonists Blunt Platelet Release of CD40 Ligand and Thromboxanes," Blood 104:1361-1368 (2004) and Ray et al. "Peroxisome Proliferator-activated Receptor Gamma and Retinoid X Receptor Transcription Factors are Released from Activated Human Platelets and Shed in Microparticles," Thromb Haemost 99:86-95 (2008), each of which is hereby incorporated by reference in its entirety). On average, 5.5×10 (Ray et al., "The Peroxisome Proliferator-activated Receptor Gamma (PPARγ) Ligands 15-deoxy-Delta12,14-prostaglandin J2 and Ciglitazone Induce Human B Lymphocyte and B Cell Lymphoma Apoptosis by PPARγ-independent Mechanisms, J Immunol 177:5068-5076 (2006), which is hereby incorporated by reference in its entirety) platelets/unit of blood were obtained, and the platelet purity was greater than 99%.

Platelet Staining and Collagen-Induced Functional Assays

Platelets were isolated from the Meg-01 cells and human blood as described above. Both normal human platelets and Meg-01-derived platelets were stained with annexin V-FITC then treated with 10 µg/ml of collagen for 15 min. Cells were analyzed for collagen-induced annexin V binding and change in size and shape by flow cytometry. Platelets were isolated from primary human megakaryocytes and primary mouse megakaryocytes as described above. Primary human platelets were stained with CD41-FITC and primary mouse platelets were stained with CD61-PE then treated with 10 µg/mL of collagen. Cells were analyzed for collagen-induced CD61/CD41 upregulation and change in size and shape using flow cytometry.

Phalloidin Staining

Cells were fixed and permeabilized with 0.1% triton-100 for 1 h at room temperature (RT). Subsequently, cells were blocked with 1% bovin serum albumin (BSA) in PBS-Tween 20 (0.1%) for 1 h at RT then stained with phalloidin-Alexa Fluor 488 (Invitrogen, 1:200) at RT for 2 h. Cells were mounted and visualized using an Olympus BX51 light microscope (Olympus, Melville, N.Y.).

Transmission Electron Microscopy

Cells were fixed for 4 h in 2.5% glutaraldehyde in 0.1 M sodium cacodylate buffer. Post-fixation cells were placed in 1% osmium tetroxide in phosphate buffer, dehydrated in ethanol, embedded in EPON/Araldite epoxy resin and analyzed on a Hitachi H-7100 electron microscope.

Platelet Spreading

Coverslips were coated with 100 µg/mL of fibrinogen for 1 h and blocked with 0.5 mg/mL BSA for 1 h. Platelets were added to the fibrinogen-coated coverslips in Tyrode's buffer and fixed with glutaraldehyde, post-fixed with 1% osmium tetroxide, and dehydrated. Platelets were then coated with a gold/palladium film. Images were acquired using the Zeiss-Leo 982 FE-SEM (scanning electron microscope).

PPARγ Gene Reporter Analysis

Meg-01 cells were plated at a density of $1.6 \times 10^7$ cells per well in a E-well plate and transfected, using lipofectamine LTX (Invitrogen), with a PPRE (Peroxisome Proliferator Response Element)-luciferase reporter plasmid containing three copies of the ACO-PPRE (a gift from Dr. B. Seed, Massachusetts General Hospital, Boston, Mass.). Cells were then treated with 10 µM 15d-$PGJ_2$, 9,10 dihydro-15d-$PGJ_2$, or rosiglitazone 24 h post-transfection. Transfection efficiency was determined by transfecting the cells with green fluorescent protein (GFP) plasmid and determining the percentage of cells that were GFP+ by flow cytometry. All cell treatment groups exhibited similar transfection efficiencies. Luciferase activity was assessed 24 h after ligand treatment using the Promega Luciferase Assay System, and relative light units (RLU) were determined using a Lumicount Microplate Luminometer (Packard Instrument Co., Meriden, Conn.).

Construction of Lentiviral Vector Expressing PPARγ siRNA

A 19 by target sequence was selected to knock down PPARγ. PPARγ was cloned downstream of the RNA polymerase III U6 promoter and subcloned into a FG12 lentiviral vector which expresses green fluorescent protein (GFP) under the Ubiquitin C promoter. HEK 293 cells expressing this siRNA PPARγ had reduced PPARγ protein levels. To make the lentivirus, HEK 293 cells were co-transfected with 3 plasmids: the envelope vector (CMV-VSVG), the transfer vector (FG12-shRNAPPAR), and the packaging construct (pCMVΔ89.2 (gag/pol proteins)). Viral supernatants were collected every 8 h for 2 days and concentrated by ultracentrifugation at 50,000×g for 2 h at 4° C. using a Beckman SW 28 rotor. Viral titers were determined by infection of HeLa cells with serial dilutions of the viral stocks. Meg-01 cells were infected at a multiplicity of infection (MOI) of 20. After 48 h, approximately 56% of the PPARγ siRNA cells were transduced as determined by flow cytometry. The GFP positive (+) cells were then sorted by FACS and grown in RPMI with 5% FBS.

Western Blotting for PPARγ

Western blot for PPARγ was performed as previously described (Akbiyik et al., "Human Bone Marrow Megakaryocytes and Platelets Express PPARγ, and PPARγ Agonists Blunt Platelet Release of CD40 Ligand and Thromboxanes," Blood 104:1361-1368 (2004) and Ray et al. "Peroxisome Proliferator-activated Receptor Gamma and Retinoid X Receptor Transcription Factors are Released from Activated Human Platelets and Shed in Microparticles," Thromb Haemost 99:86-95 (2008), each of which is hereby incorporated by reference in its entirety). Briefly, a rabbit anti-human polyclonal primary antibody against PPARγ (Biomol) was added at a 1:1000 dilution in 5% nonfat milk for 1 h at RT. The secondary Ab (Jackson ImmunoResearch Laboratories) was added at a 1:10000 dilution for 1 h in 2.5% nonfat milk. Membranes were visualized with enhanced chemiluminescence (ECL, Pierce).

Reactive Oxygen Species Production

Ten µM carboxy-$H_2$DCFDA was added to cells for 20 min at RT. The cells were washed and immediately analyzed by flow cytometry. Five µM of MitoSOX Red dye in HBSS containing $Mg^{2+}$ and $Ca^{2+}$ was added to the cells for 15 min at 37° C. The cells were washed in HBSS and analyzed by flow cytometry.

DNA Content Analysis

Cells were fixed in 95% ethanol, treated with RNAse (Sigma) followed by 20 µg/mL propidium iodide (Sigma) to stain DNA, and analyzed by flow cytometry.

Megakaryocyte Progenitor (Meg-CFCs) Assay

Primary mouse bone marrow cells were suspended in IMDM at a concentration of $8 \times 10^6$ cells/mL. Two-hundred thousand cells were plated in IMDM supplemented with 20% BIT9500, 0.2% 2-mercaptoethanol, 2% Glutamax, and 20% Cellgro-$H_2$0 (Mediatech, Herndon, Va.) and cultured with rhTPO (50 ng/mL), IL-3 (10 ng/mL) (Preprotech, Rocky Hill, N.J.), IL-6 (20 ng/mL) (Preprotech), IL-11 (Preprotech) (50 ng/mL), and collagen at 37° for 7 days (Tober et al., "The Megakaryocyte Lineage Originates from Hemangioblast Precursors and is an Integral Component Both of Primitive and of Definitive Hematopoiesis," *Blood* 109:1433-1441 (2007), which is hereby incorporated by reference in its entirety). Collagen gels were dehydrated, fixed, and labeled with GPIbβ and GPV, modified by ABC (Vector Labs, Burlingame, Calif.), and developed in Vector Red (Vector Labs). Meg-CFC were defined by their ability to generate colonies containing at least three megakaryocytes.

Irradiation-Induced Thrombocytopenia

Seven or 8-week-old male C57BL/6 mice (Jackson Laboratories) were either exposed to 5 Gy cesium ($Cs^{137}$) total body irradiation (TBI) using a Model 8114 6000 Curie Shepherd $Cs^{137}$ irradiator (approximately 3200 Curie sealed $Cs^{137}$ source) with a dose rate of 177.9 Gy/min or left unexposed. Mice (n=4) received intravenous injections of vehicle (8% DMSO) or 15d-$PGJ_2$ (1 mg/kg) or CDDO-Me (250 μg/kg) for 4 consecutive days from day 1 (days 1, 2, 3 and 4 postirradiation). Blood was obtained from the aorta or the orbital sinus. Platelets were counted prior to radiation exposure and after radiation exposure on day 10, day 22, and day 31 in Example 7, or days 4, 10, 16, and 21 in Example 9 using the Heska® CBC-Diff™ Veterinary Analyzer (Fort Collins, Colo.). Data are expressed as average platelet counts from two separate experiments. For the unirradiated mice, platelets were counted on day 4, day 10, and day 15 in Example 7 or on the same days in Example 9.

Statistical Analysis

Results are expressed as the mean±standard deviation (SD). Statistical analysis was performed using a paired, two-tailed Student's t test with $P<0.05$ deemed as statistically significant. All experiments were repeated at least 3 times unless otherwise stated.

Example 1

Small Electrophilic Molecules Induce Platelet Formation

Figure 1B:
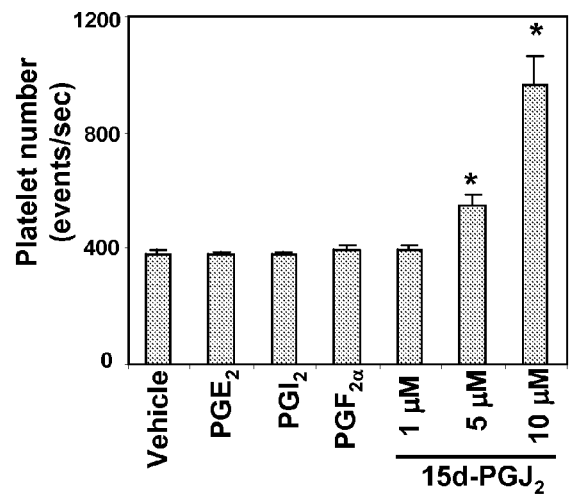
Figure 1C:
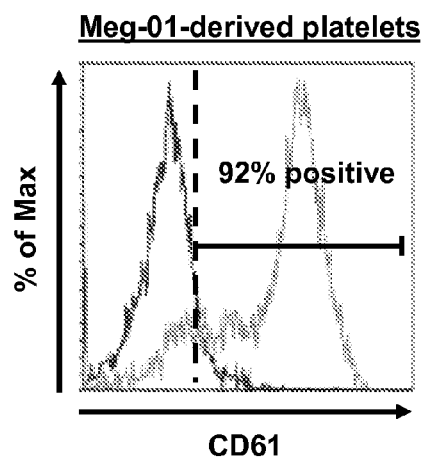

Initial studies demonstrated that three well-described megakaryocytic cell lines (Meg-01, M07e, Dami) all increased platelet production after exposure for 24 h to 15d-$PGJ_2$ (FIG. 1A). Further studies were completed on Meg-01 cells, as this cell produces platelets similar in structure and function to freshly isolated human platelets (Takeuchi et al., "Production of Platelet-like Particles by a Human Megakaryoblastic Leukemia Cell Line (MEG-01)," *Exp Cell Res* 193:223-226 (1991), which is hereby incorporated by reference in its entirety. Treatment of Meg-01 cells with increasing concentrations of 15d-$PGJ_2$ caused a dose-dependent increase in platelet production (FIG. 1B). However, not every type of prostaglandin enhanced platelet production. For example, $PGE_2$, $PGI_2$ and $PGF_{2\alpha}$ failed to enhance platelet production (FIG. 1B). Platelets derived from Meg-01 cells express the platelet marker CD61 (glycoprotein IIIa, FIG. 1C).

Figure 1D:
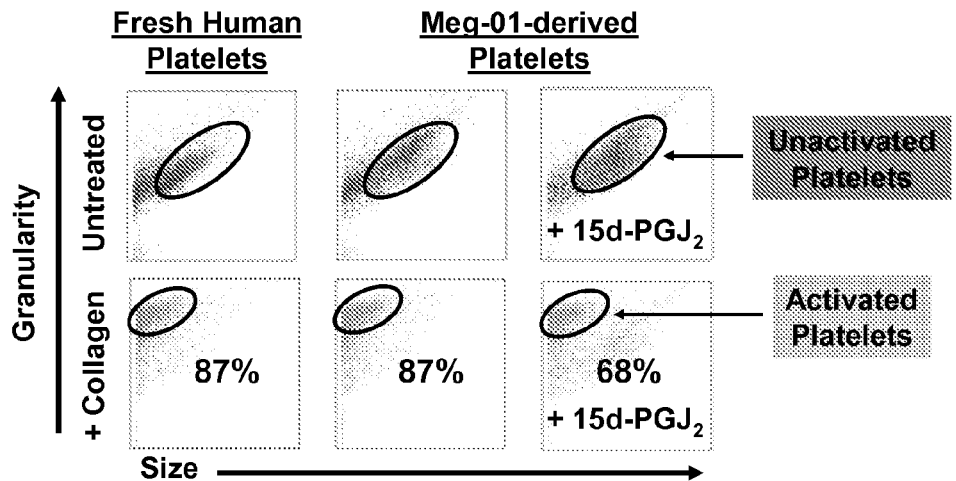
Figure 1E:
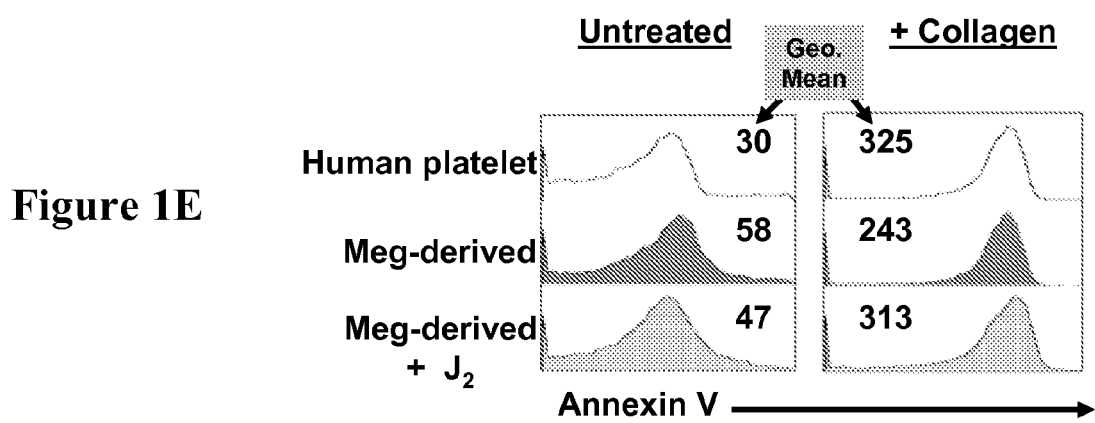

It was next determined whether the platelets produced by 15d-$PGJ_2$ treatment were responsive to known activators. In normal human platelets, collagen promotes shape-change and phosphatidylserine becomes highly expressed on the surface of platelets (Ramstrom et al., "Platelet Phosphatidylserine Exposure and Procoagulant Activity in Clotting Whole Blood—Different Effects of Collagen, TRAP and Calcium Ionophore A23187," *Thromb Haemost* 89:132-141 (2003); Labios et al., "Effect of Eprosartan on Cytoplasmic Free Calcium Mobilization, Platelet Activation, and Microparticle Formation in Hypertension," *Am J Hypertens* 17:757-763 (2004), each of which is hereby incorporated by reference in its entirety). Therefore, annexin V staining was used to distinguish platelets from apoptotic bodies and as a quantitative measure of platelet activation. Meg-01 cells were untreated or treated with 15d-$PGJ_2$, and the Meg-01 derived-platelets were isolated and treated with collagen. Following collagen activation, Meg-01-derived platelets changed size and shape, as indicated by a decrease in forward scatter (size) and an increase in side scatter (granularity) (FIG. 1D). In addition, collagen increased the binding of annexin V in both Meg-01-derived platelets and normal human platelets (FIG. 1E). These data indicate that Meg-01-derived platelets and normal human platelets have similar responses to collagen stimulation.

Morphological changes, characteristic of megakaryopoiesis, in Meg-01 cells were evident within 1-2 h of 15d-$PGJ_2$ treatment, as revealed by staining for filamentous (f)-actin (FIGS. 1F-G). Arrows in FIG. 1G show actin bundles protruding from the cell membrane. The formation of these protrusions are associated with megakaryopoiesis, as actin is found in proplatelet extensions and is important for the bending and bifurcation of the branches (Italiano et al., "Blood Platelets are Assembled Principally at the Ends of Proplatelet Processes Produced by Differentiated Megakaryocytes," *J Cell Biol* 147:1299-1312 (1999); Rojnuckarin et al. "Actin Reorganization and Proplatelet Formation in Murine Megakaryocytes: the Role of Protein Kinase Calpha," *Blood* 97:154-161 (2001), each of which is hereby incorporated by reference in its entirety). These membrane protrusions were absent in untreated Meg-01 cells (FIG. 1F). Meg-01 cells were also analyzed by transmission electron microscopy (TEM). Within 24 h of 15d-$PGJ_2$ treatment, Meg-01 cells exhibited structural characteristics consistent with differentiating cells, such as granule formation (g), a horseshoe-shaped nucleus (n), and the elongation of cytoplasmic extensions (c) (FIG. 1I). FIG. 1I confirms the presence of the cytoplasmic extensions seen with phalloidin staining. These phenotypic changes are absent in untreated cells (FIG. 1H).

Example 2

15d-$PGJ_2$ Promotes Platelet Production from Cultured Mouse Megakaryocytes

Figure 2A:
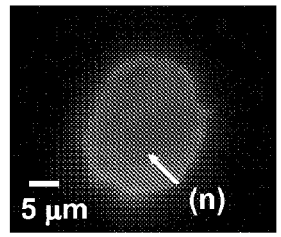
FIG. 2A-E show 15d-$PGJ_2$ enhances platelet production from mouse megakaryocytes in vitro. Bone marrow isolated from C57BL/6 mice was cultured for days in the presence of rhTPO. On day 5 of culture, cells were treated with vehicle or 15d-$PGJ_2$ (10 μM) for 24 h. Cells were photographed in culture and platelet production was analyzed by flow cytometry.
Figure 2A:
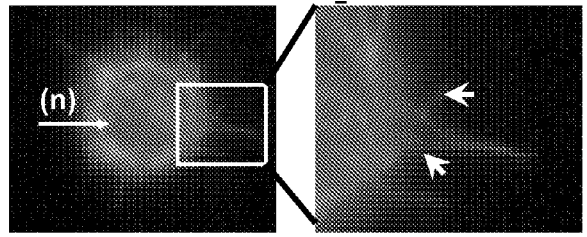
Figure 2A:
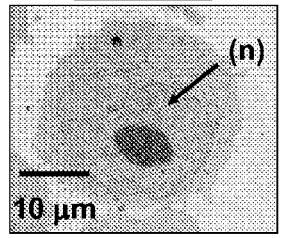
Figure 2A:
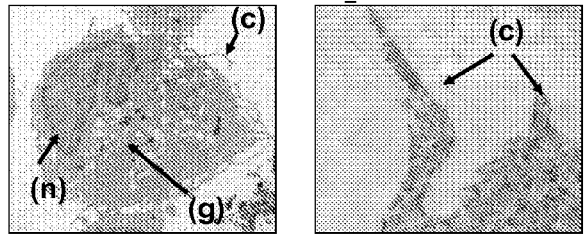
Figure 2A:
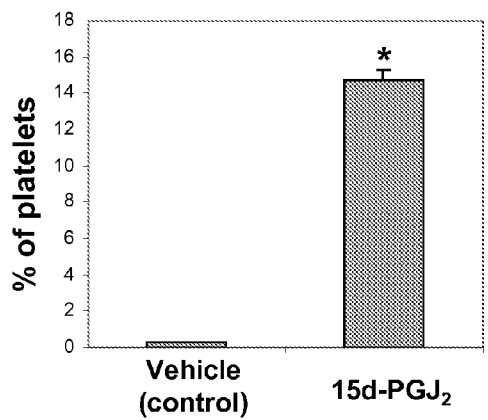
Figure 2B:
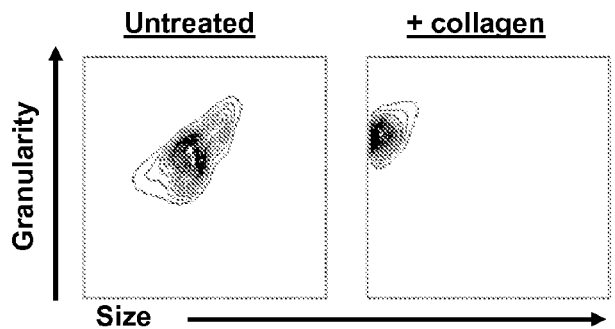
Figure 2C:
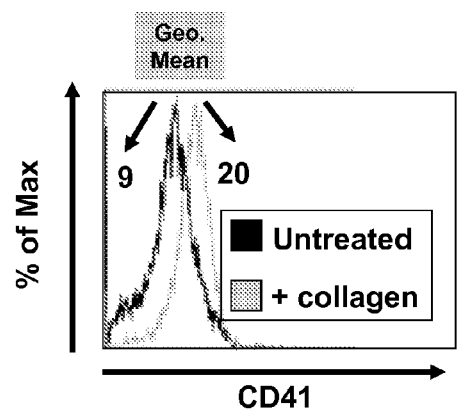
Figure 2D:
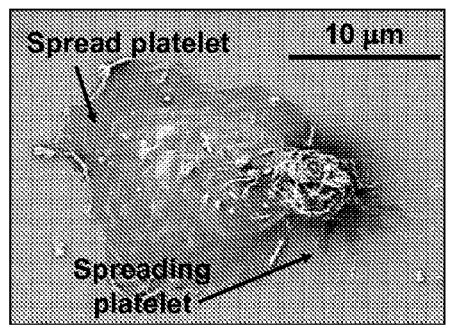
Figure 2E:
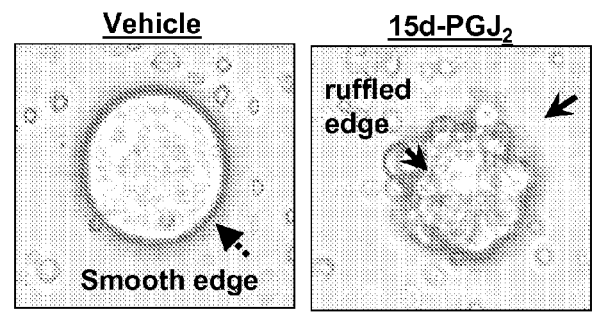

To evaluate whether 15d-$PGJ_2$ affects platelet production from normal mouse megakaryocytes, primary mouse bone marrow cells were cultured for 5 days with rhTPO to promote megakaryocyte enrichment and maturation. Following culture, bone marrow cells were treated with 15d-$PGJ_2$ for 24 h. 15d-$PGJ_2$ increased the percentage of CD61+ platelets in culture by ~14% (FIG. 2A). These mouse bone marrow-derived platelets exhibited normal responses to collagen, as they changed shape (decrease in size and increase in granularity) and increased their surface expression of CD41 (GPIIb, FIGS. 2B-C). Geometric mean fluorescence intensity increased from 9 to 20 after collagen treatment. Mouse bone marrow culture-derived platelets show functionality, as they spread in response to fibrinogen (FIG. 2D). 15d-$PGJ_2$ also induced the appearance of ruffled edges on the megakaryocytes, commonly observed during membrane blebbing of platelets, whereas vehicle-treated megakaryocytes exhibited a smooth surface (FIG. 2E).

Example 3

15d-$PGJ_2$ Promotes Platelet Production from Cultured Human Megakaryocytes

Figure 3A:
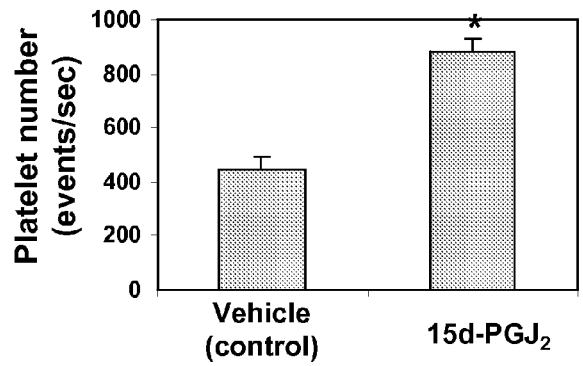
FIGS. 3A-E show that megakaryocytes generated from human cord blood-derived CD34+ cells in vitro exhibit increased platelet production with 15d-$PGJ_2$ treatment. CD34+ cells cultured in the presence of rhTPO for 14 days are 92% positive for CD61. CD61 expressing cells generated from cord blood were treated with vehicle or 15d-$PGJ_2$ (10 μM) for 24 h and cells were photographed in culture and platelet production was analyzed by flow cytometry.
Figure 3B:
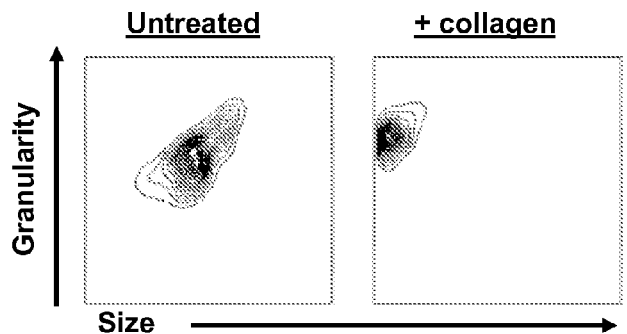
Figure 3C:
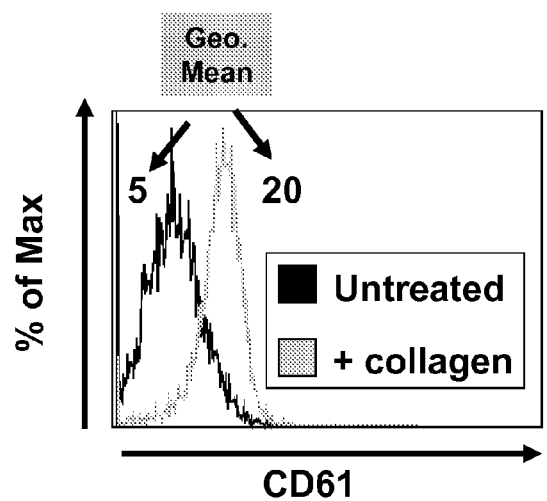
Figure 3D:
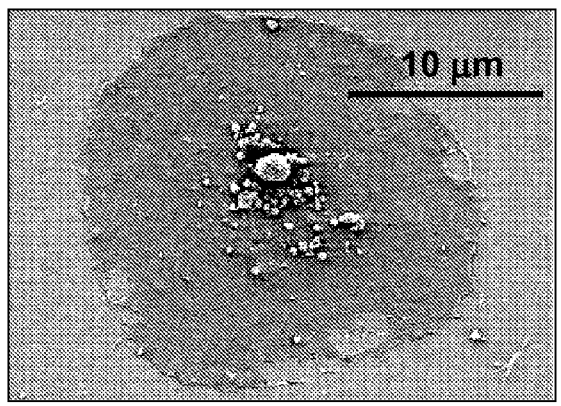
Figure 3E:
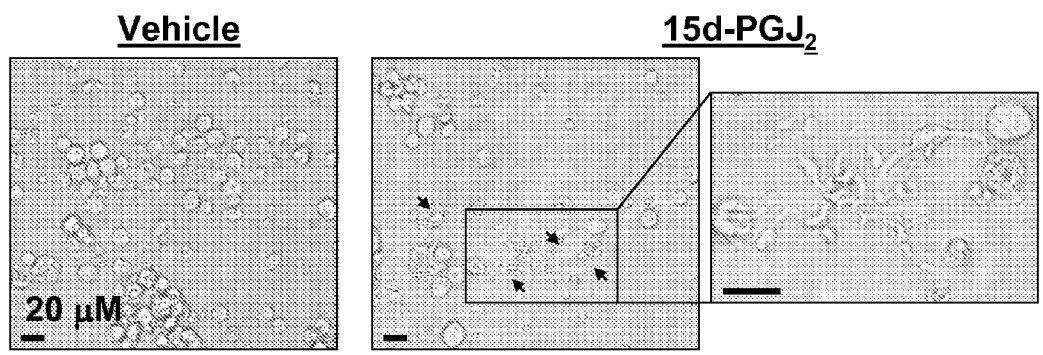

Cord blood-derived CD34+ cells (99% pure) were cultured for 14 days with rhTPO, at which time more than 90% of the cells expressed CD61. The cultures consisted of a mixed population of both immature and mature megakaryocytes as determined by ploidy observed by Diff-Quik staining. These CD61+ cells were then treated with 15d-PGJ$_2$ (10 µM) for 24 h and platelet production was assessed by flow cytometry. Treatment with 15d-PGJ$_2$ doubled the number of platelets generated from these human megakaryocytes as determined by presence of the platelet marker CD61 and the absence of DNA (FIG. 3A). Flow cytometric data showed that human culture-derived platelets exhibited normal responses to collagen, as they changed shape (decrease in size and increase in granularity) and increased their surface expression of CD61 (FIGS. 3B-C). Geometric mean fluorescence intensity increased from 5 to 20 after collagen treatment. In addition, these culture-derived platelets showed functionality, as they spread in response to fibrinogen (FIG. 3D). 15d-PGJ$_2$ also induced proplatelet formation (FIG. 3E).

Example 4

Platelet Production Induced by 15d-PGJ$_2$ is Independent of PPARγ

Figure 4A:
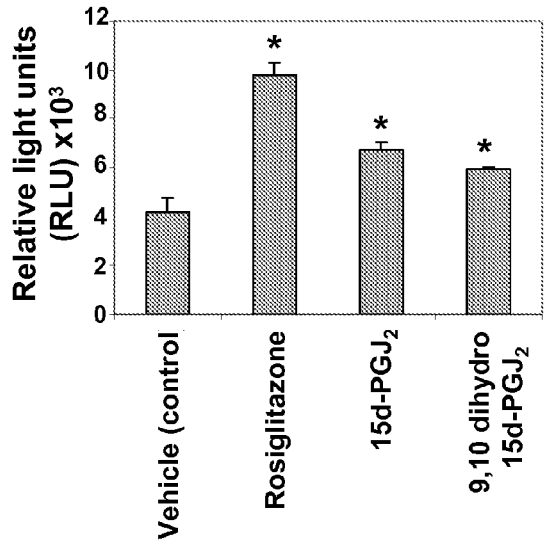
FIGS. 4A-D show platelet production from Meg-01 cells by 15d-PGJ$_2$ is independent of PPARγ.
Figure 4B:
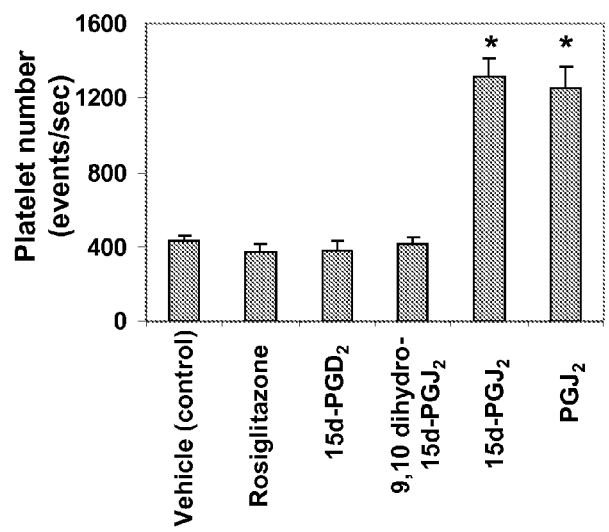
Figure 4C:
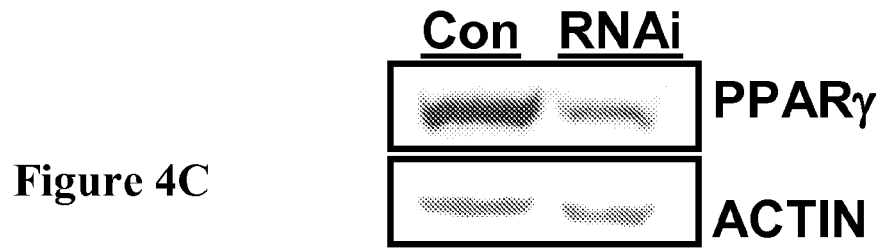
Figure 4D:
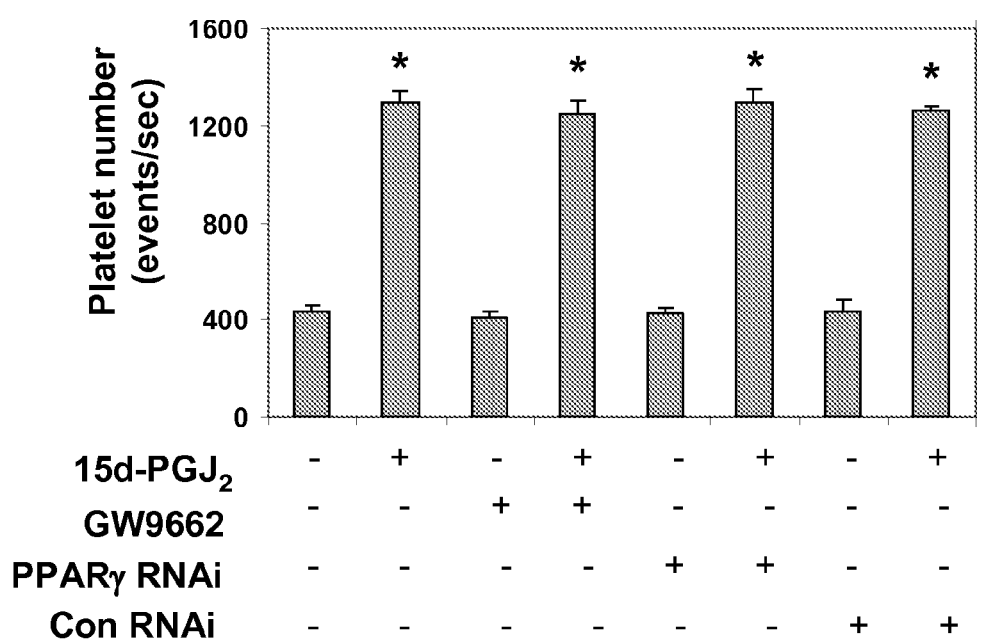

Whether 15d-PGJ$_2$ enhanced platelet production was PPARγ-dependent or independent was investigated next. All PPARγ ligands tested (15d-PGJ$_2$, 9,10 dihydro-15d-PGJ$_2$, and rosiglitazone) activated PPARγ (FIG. 4A). Despite this, only the electrophilic prostaglandins (PGJ$_2$ and 15d-PGJ$_2$) enhanced Meg-01 platelet production (FIG. 4B). Non-electrophilic thiazolidinedione-type drugs such as rosiglitazone and the non-electrophilic prostaglandins: 9,10 dihydro-15d-PGJ$_2$ and 15d-PGD$_2$ failed to enhance platelet production. (FIG. 4B). This indicates that the effects of these agents are independent of PPARγ. The involvement of PPARγ in the platelet generating effects of 15d-PGJ$_2$ was further analyzed by infecting Meg-01 cells with a PPARγ siRNA lentivirus (FIG. 4C). As shown in FIG. 4D, knocking down PPARγ protein failed to attenuate the platelet-enhancing effects of 15d-PGJ$_2$. In addition, the ability of 15d-PGJ$_2$ to enhance platelet production was not blocked by the small molecule, irreversible PPARγ antagonist, GW9662 (Leesnitzer et al., "Functional Consequences of Cysteine Modification in the Ligand Binding Sites of Peroxisome Proliferator Activated Receptors by GW9662," *Biochemistry* 41:6640-6650 (2002), which is hereby incorporated by reference in its entirety). This further supports that the effects of 15d-PGJ$_2$ are PPARγ-independent.

Example 5

15d-PGJ$_2$ Induces Reactive Oxygen Species Formation

15d-PGJ$_2$ can act independently of PPARγ by modulating cellular redox status (Atsmon et al., "Formation of Thiol Conjugates of 9-deoxy-delta 9, delta 12(E)-prostaglandin D2 and Delta 12(E)-prostaglandin D2," *Biochemistry* 29:3760-3765 (1990); Shibata et al., "Thioredoxin as a Molecular Target of Cyclopentenone Prostaglandins," *J Biol Chem* 278: 26046-26054 (2003) and Nosjean et al., "Natural Ligands of PPARγ: Are Prostaglandin J(2) Derivatives Really Playing the Part?," *Cell Signal* 14:573-583 (2002), each of which is hereby incorporated by reference in its entirety). Subsequent experiments were performed to address whether 15d-PGJ$_2$ and other prostaglandins alter intracellular ROS levels in megakaryocytes. Carboxy-H$_2$DCFDA was used to detect a broad range of oxidants, including superoxide, peroxynitrate, hydrogen peroxide, and nitric oxide (NO). Flow cytometric analysis (FIG. 5A) demonstrates an increase in the percentage of Meg-01 cells that express ROS from 52% to 91% after 1 h and 97% after 6 h of 15d-PGJ$_2$ treatment. The non-electrophilic compounds, 9,10 dihydro-15d-PGJ$_2$ and 15d-PGD$_2$, failed to increase the percentage of cells generating ROS. However, another electrophilic prostaglandin, PGJ$_2$, also increased the percentage of cells expressing ROS (65% at 1 h and 76% at 6 h).

In addition to total intracellular ROS, the ability of different prostaglandins to increase mitochondrial superoxide levels using MitoSOX Red was investigated next. MitoSOX Red is a live-cell permeant indicator that is rapidly targeted to the mitochondria where it reacts with superoxides and binds to nucleic acids, resulting in fluorescence (Robinson et al., "Selective Fluorescent Imaging of Superoxide In Vivo Using Ethidium-based Probes," *Proc Natl Acad Sci USA* 103: 15038-15043 (2006), which is hereby incorporated by reference in its entirety). Flow cytometric analysis (FIG. 5B) demonstrates an increase in the percentage of Meg-01 cells that produce mitochondrial superoxide at 1 h (43%) and 6 h (31%) after 15d-PGJ$_2$ treatment (10 uM). Similar to carboxy-H$_2$DCFDA analysis, the non-electrophilic 9,10 dihydro-15-PGJ$_2$ and 15d-PGD$_2$ failed to increase the percentage of cells generating mitochondrial superoxide. However, the electrophilic PGJ$_2$, also increased the percentage of cells expressing superoxide at 1 h (33%) and 6 h (25%). Thus, electrophilic prostaglandins induce ROS in Meg-01 cells.

The Meg-01 studies were extended by examining intracellular ROS production in primary human megakaryocytes in response to 15d-PGJ$_2$ and 9,10 dihydro-15d-PGJ$_2$. Flow cytometric analysis (FIG. 5C) demonstrates an increase in the percentage of ROS positive cells in the 15d-PGJ$_2$ cultures after carboxy-H$_2$DCFDA staining and Mitosox Red staining at 1 h and 6 h.

Example 6

Antioxidants Attenuate Platelet Production

The effects of 15d-PGJ$_2$ on platelet production are partially reversed with pretreatment using thiol antioxidants such as GSH-EE and NAC. Meg-01 cells and primary human megakaryocytes were pretreated with 5 mM of GSH-EE or 1 mM of NAC for 2 h and extensively washed prior to 15d-PGJ$_2$ addition. After 24 h, cells were stained for CD61 expression and platelet number was evaluated. Flow cytometric data (FIG. 5D) reveal that both GSH-EE and NAC attenuate 15d-PGJ$_2$-induced platelet production by reducing the number of platelets produced to approximately control levels. Collectively, these data indicate that the production of ROS is important for platelet production from megakaryocytes.

Example 7

15d-PGJ$_2$ Increases Megakaryocyte Ploidy and Proplatelet Formation

Figure 6A:
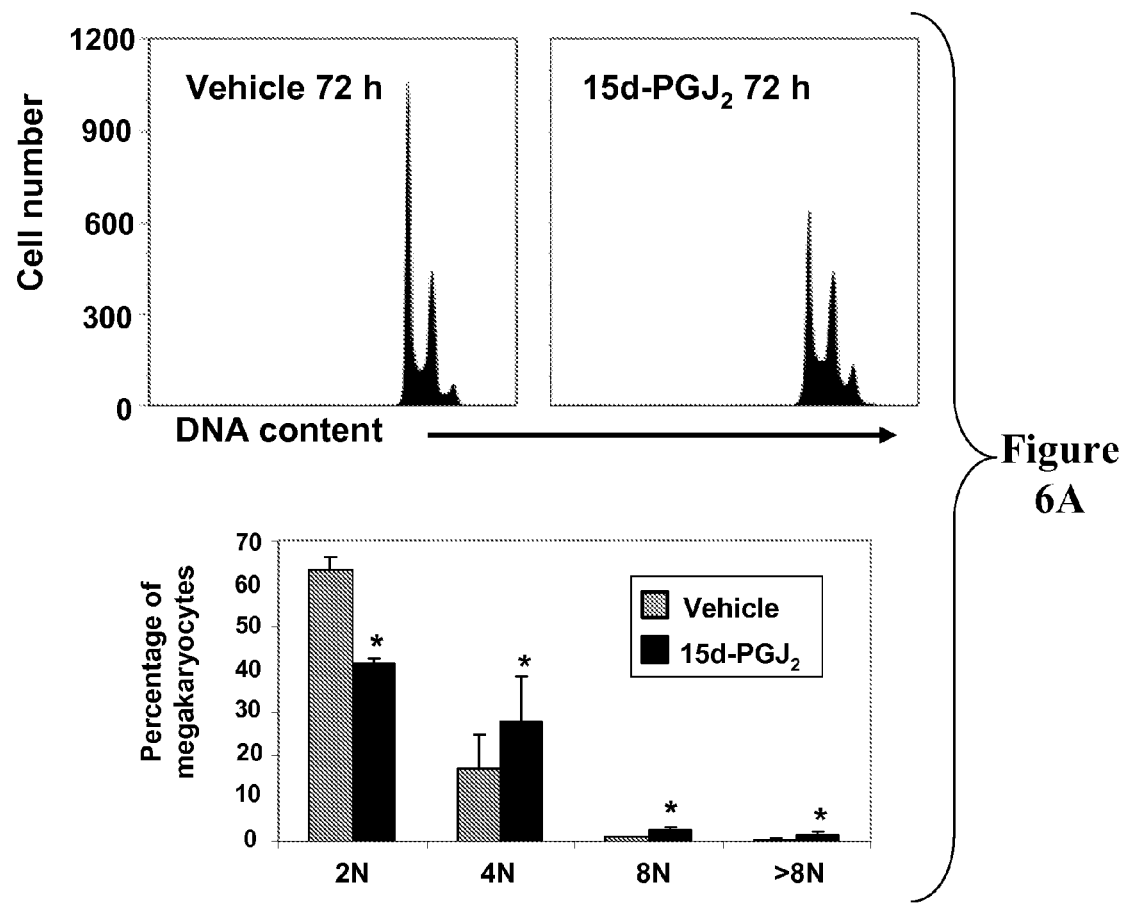
FIGS. 6A-E show 15d-PGJ$_2$ augments DNA content and enhances proplatelet formation.
Figure 6B:
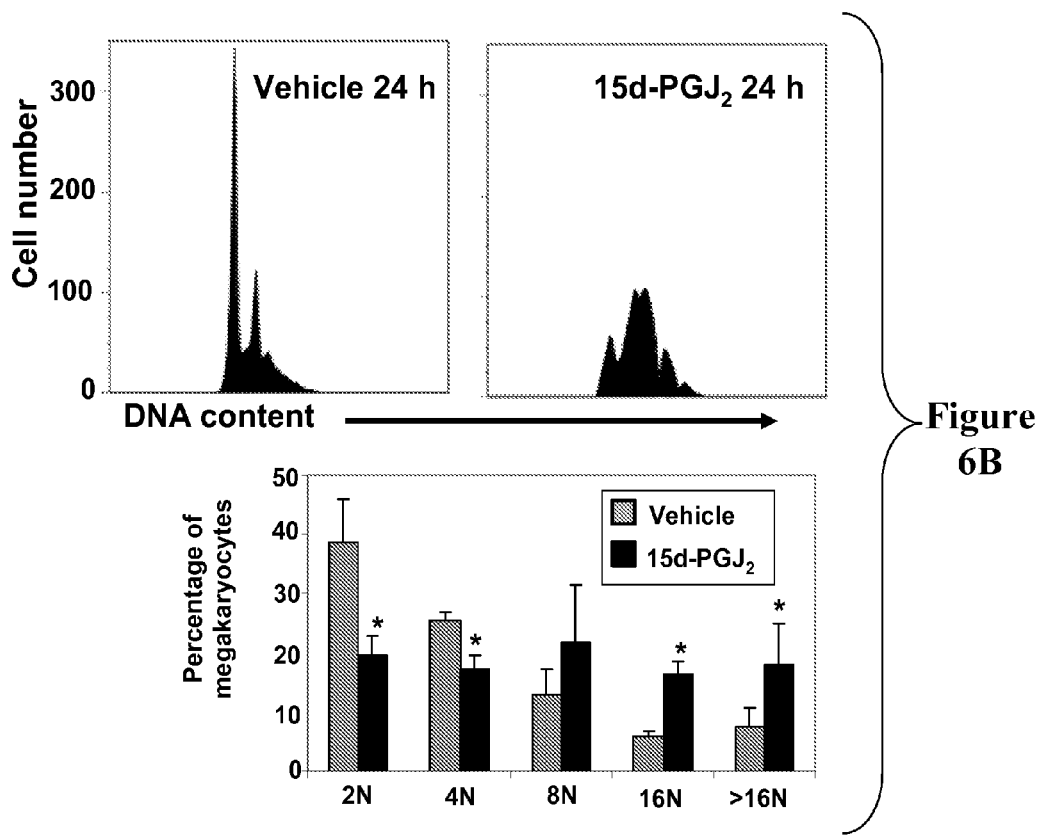
Figure 6D:
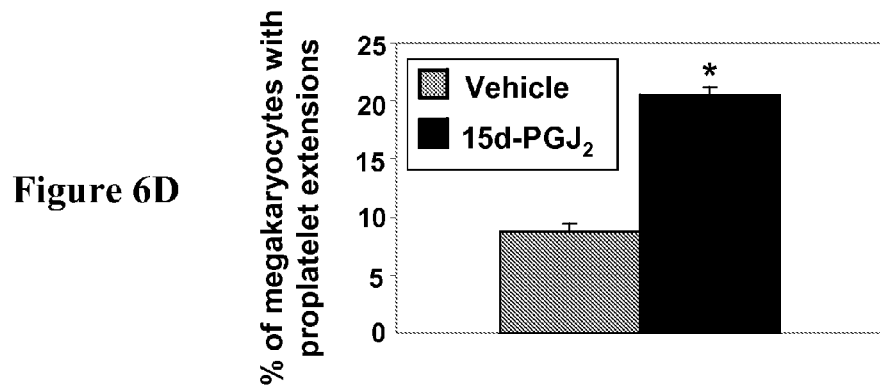
Figure 6C:
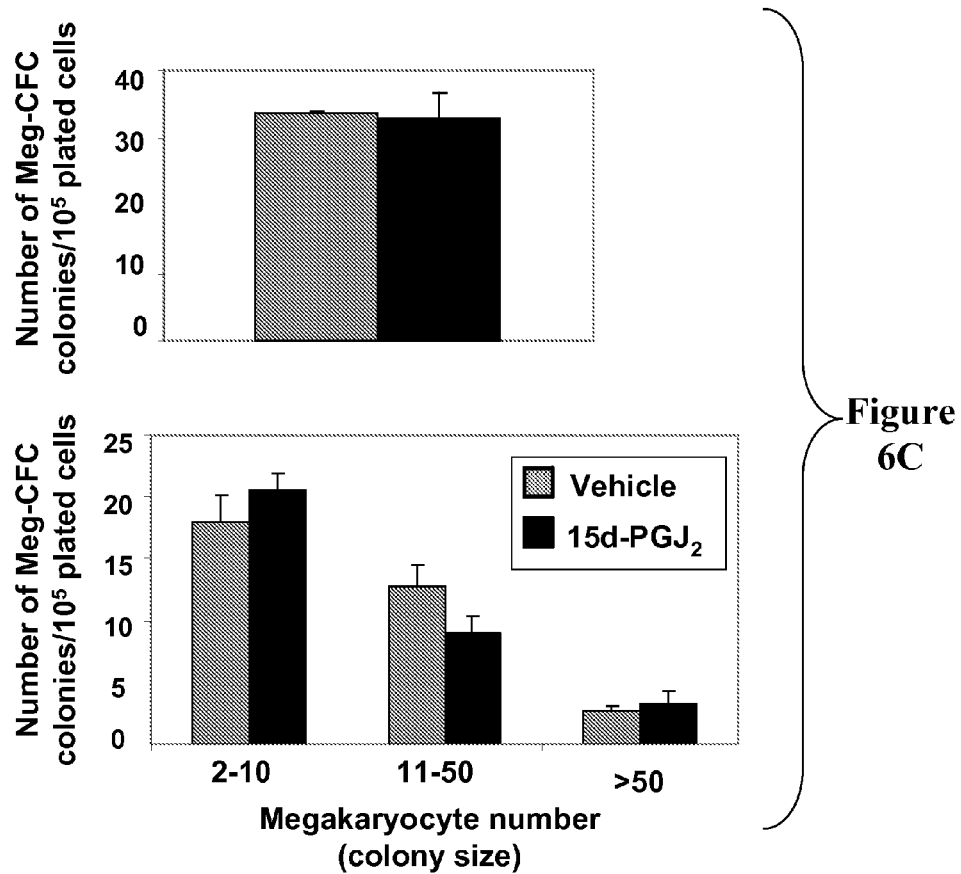
Figure 6E:
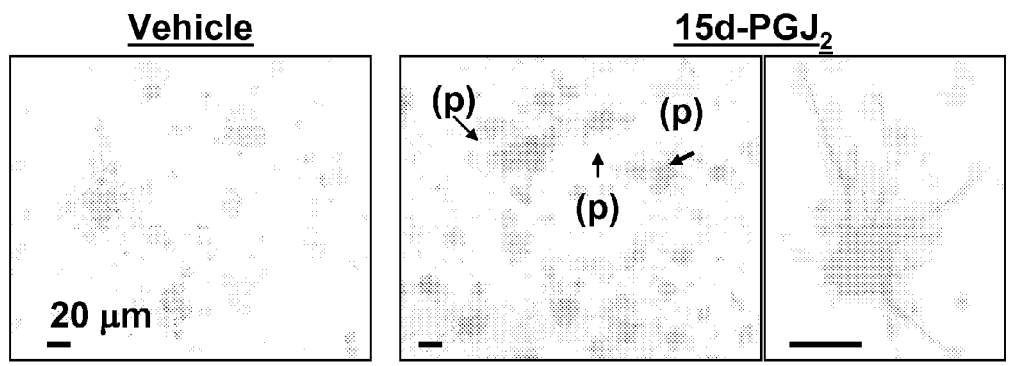

To determine the mechanism of increased platelet production, the effect of 15d-PGJ$_2$ on megakaryocyte colony formation and maturation was examined. Meg-01 cells were treated with 15d-PGJ$_2$ for 24, 48, or 72 h. Although DNA content was unchanged at 24 h and 48 h, histograms show that 15d-PGJ$_2$ addition increased DNA content in Meg-01 cells by 72 h (FIG. 6A). In addition, DNA histograms show that 15d-PGJ$_2$ increased DNA content in primary mouse megakaryocytes by 24 h (FIG. 6B). To determine the effect of 15d-PGJ$_2$ on early stage thrombopoiesis, primary mouse bone marrow cells were harvested from mice that were injected with 1 mg/kg of 15d-PGJ$_2$ or 1 mg/kg of vehicle for two consecutive days. After 7 days of culture, Meg-CFCs were identified by labeling with GPV and GPIbβ. 15d-PGJ$_2$ did not influence megakaryocyte colony number or colony size (FIG. 6C), however, 15d-PGJ$_2$ significantly augmented the percentage of megakaryocytes producing proplatelets (FIG. 6D-E).

Example 8

15d-PGJ$_2$ Enhances Platelet Recovery Following Ionizing Radiation

Figure 7A:
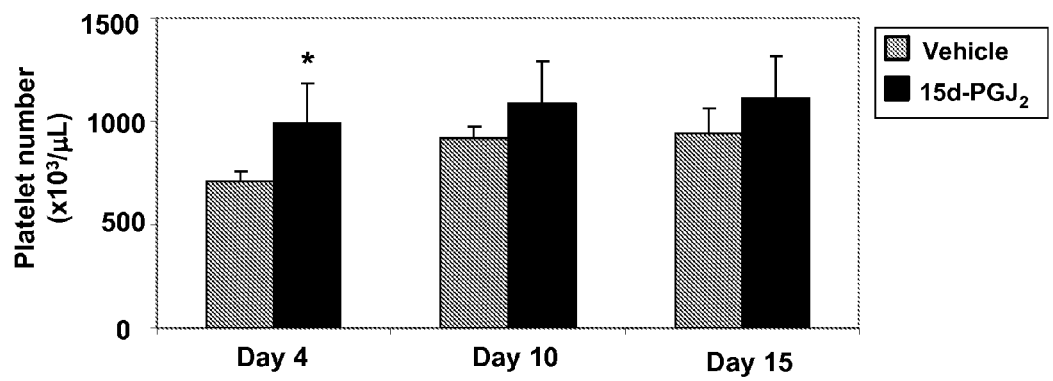
FIG. 7A-B show that 15d-PGJ$_2$ enhances platelet number in vivo and accelerates recovery of platelets following ionizing radiation.
Figure 7B:
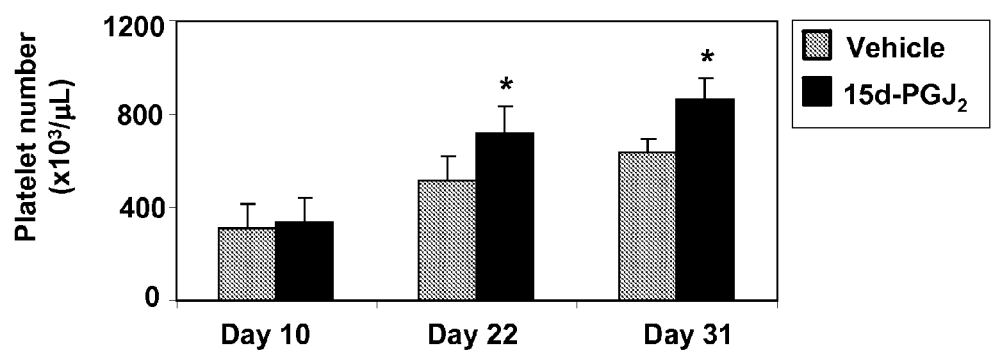

Mice that received intravenous injections of 15d-PGJ$_2$ for 4 consecutive days had higher platelet numbers when compared with mice that received vehicle (FIG. 7A). To evaluate the effect of 15d-PGJ$_2$ on platelet counts in a model of thrombocytopenia, mice were exposed to Cs$^{137}$ (5 Gy). Mice exhibited a platelet nadir at approximately 10 days following irradiation (approximately 250,000/μL). The mice that received intravenous injections of 15d-PGJ$_2$ for 4 consecutive days exhibited accelerated platelet recovery on day 22 and day 31 when compared to the vehicle mice (FIG. 7B). Platelet numbers completely recovered (approximately 800,000/μL) by day 31 in the 15d-PGJ$_2$ treated mice. There were no differences in weight between vehicle-treated mice and 15d-PGJ$_2$-treated mice.

Example 9

CDDO-Me Increases Megakaryocyte Proplatelet Formation

Figure 8:
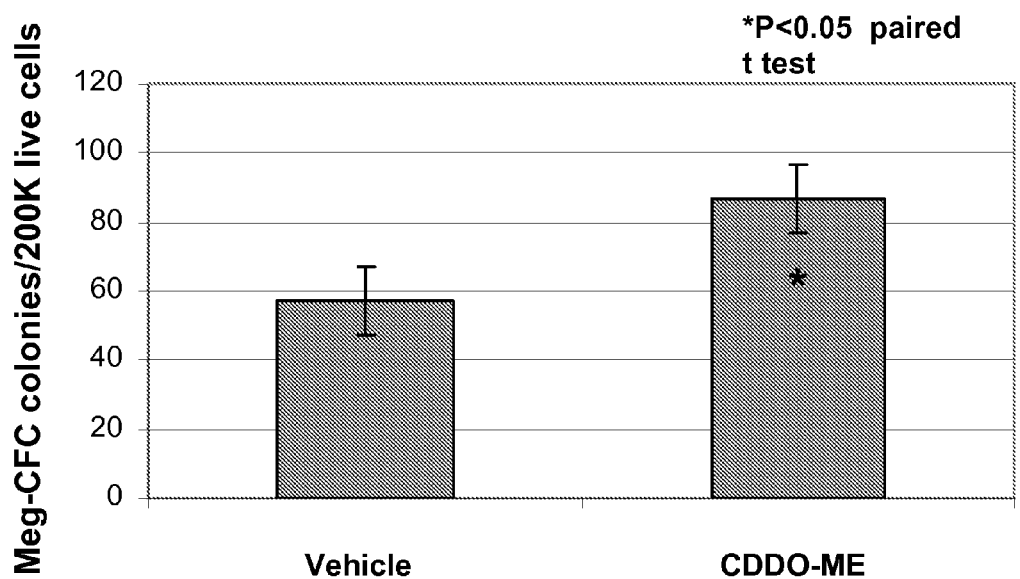
FIG. 8 is a graph that illustrates the effects of in vivo administration of CDDO-Me on mouse megakaryocyte progenitor (Meg-CFC) colony formation. Normal mice were given 250 μg/kg of CDDO-Me for three consecutive days, bone marrow was harvested, and bone marrow cells were plated for a colony forming assay on day 4. CDDO-Me significantly enhanced Meg-CFC colony formation as compared to vehicle control.

The effect of another family of electrophilic compounds to enhance on early stage thrombopoiesis using the megakaryocyte colony formation assay of Example 7. To determine the effect of CDDO-Me, primary mouse bone marrow cells were harvested from mice that were injected with 250 μg/kg of CDDO-Me or 250 μg/kg of vehicle for three consecutive days. After 7 days of culture, Meg-CFCs were identified by labeling with GPV and GPIbβ. CDDO-Me significantly augmented the percentage of megakaryocytes producing proplatelets (FIG. 8).

Example 10

CDDO-Me Enhances Platelet Recovery Following Ionizing Radiation

The ability of another family of electrophilic compounds was examined for enhancement of platelet recovery following ionizing radiation. Using the same model from Example 8, mice were administered 250 μg/kg of CDDO-Me on the following four consecutive days (days 1-4) following exposure, and platelet counts were measured on day 4, day 10, day 16, and day 21. CDDO-Me administration significantly improved platelet counts on days 10 and 16 (FIG. 9), and increased platelet counts were also observed on day 4. This demonstrates that the tri-terpenoid electrophilic compounds, such as CDDO-Me, share with 15d-PGJ$_2$ the ability to influence platelet depletion and recovery following radiation exposure.

Discussion of Examples 1-10

Thrombocytopenia causes significant morbidity and mortality, and few therapies are useful except for transfusion. Understanding the molecular mechanisms which underlie both megakaryocyte maturation and platelet release will provide insight into new ways to enhance platelet production from their precursor cells, the megakaryocytes. The results presented herein demonstrate that several electrophilic compounds, including 15d-PGJ$_2$ and CDDO-Me, enhance platelet production from mouse and/or human megakaryocytes. The results show that ROS generation is critical for platelet production and that small electrophilic compounds, such as 15d-PGJ$_2$ and CDDO-Me, which enhance ROS, should provide therapeutic benefit in the treatment of thrombocytopenia.

Meg-01 cells undergo differentiation reflective of megakaryocyte maturation and platelet release (Takeuchi et al., "Production of Platelet-like Particles by a Human Megakaryoblastic Leukemia Cell Line (MEG-01)," *Exp Cell Res.* 193:223-226 (1991), which is hereby incorporated by reference in its entirety). The data indicate that 15d-PGJ$_2$ has a strong platelet production enhancing effect in this cell line. When Meg-01 cells were treated with 15d-PGJ$_2$ they lost their smooth rounded appearance, exhibited significant cytoplasmic protrusions, and increased their granule content (FIG. 1I). Meg-01 cells also upregulated active-caspase protein in the presence of 15d-PGJ$_2$. All these features are consistent with a megakaryocyte that is actively making platelets (Deutsch et al., "Megakaryocyte Development and Platelet Production," *Br J Haematol* 134:453-466 (2006); Junt et al., "Dynamic Visualization of Thrombopoiesis within Bone Marrow," *Science* 317:1767-1770 (2007); De Botton et al., "Platelet Formation is the Consequence of Caspase Activation Within Megakaryocytes," *Blood* 100:1310-1317 (2002), each of which is hereby incorporated by reference in its entirety). These platelets appeared to be functional, as they expressed platelet surface markers and changed shape and elevated surface levels of phosphatidylserine in response to collagen (FIG. 1D-E). Phosphatidylserine is upregulated on the surface of platelets with collagen activation and is important for blood coagulation (Ramstrom et al., "Platelet Phosphatidylserine Exposure and Procoagulant Activity in Clotting Whole Blood—Different Effects of Collagen, TRAP and Calcium Ionophore A23187," *Thromb Haemost* 89:132-141 (2003); Heemskerk et al., "Collagen but Not Fibrinogen Surfaces Induce Bleb Formation, Exposure of Phosphatidylserine, and Procoagulant Activity of Adherent Platelets: Evidence for Regulation by Protein Tyrosine Kinase-dependent Ca2+ responses," *Blood* 90:2615-2625 (1997), each of which is hereby incorporated by reference in its entirety).

The findings were expanded based on Meg-01 cells by also evaluating differentiating megakaryocytes from mouse bone marrow and from human cord blood-derived CD34+ cells. In both mouse and human cultures, more platelets were generated from megakaryocytes after 15d-PGJ$_2$ treatment. Culture-derived platelets showed similar morphological and functional features to normal human platelets. They expressed platelet-specific receptors and were activated in response to either collagen or fibrinogen. Culture-derived platelets upregulated CD61 and CD41, changed shape in response to collagen stimulation and spread on fibrinogen-coated slides. Platelet spreading is an irreversible process necessary for platelet-surface contact during hemostasis and is, therefore, a good measure of platelet function (Savage et al., "Initiation of Platelet Adhesion by Arrest onto Fibrinogen or Translocation on von Willebrand Factor," *Cell* 84:289-297 (1996), which is hereby incorporated by reference in its entirety).

A further extension of these results was performed in Examples 9 and 10, where the ability of additional electrophilic compounds to induce platelet production was assessed.

The results achieved with the tri-terpenoid CDDO-Me confirmed the results achieved with 15d-PGJ$_2$, and confirmed that the electrophilic nature of CDDO-Me and 15d-PGJ$_2$ is the critical property shared by these compounds.

15d-PGJ$_2$ is a potent PPARγ ligand (Forman et al., "15-Deoxy-delta 12,14-prostaglandin J2 is a Ligand for the Adipocyte Determination Factor PPAR Gamma," *Cell* 83:803-812 (1995), which is hereby incorporated by reference in its entirety). Although PPARγ is important in adipogenesis and inflammation (Schoonjans et al., "The Peroxisome Proliferator Activated Receptors (PPARS) and Their Effects on Lipid Metabolism and Adipocyte Differentiation," *Biochim Biophys Acta* 1302:93-109 (1996), which is hereby incorporated by reference in its entirety), recent studies confirm that PPARγ ligands influence the hematopoietic system (Greene et al., "PPARγ: Observations in the Hematopoietic System," *Prostaglandins Other Lipid Media* 62:45-73 (2000), which is hereby incorporated by reference in its entirety). Nagasawa et al. published that certain PPARγ ligands impaired erythrocyte maturation (Nagasawa et al., "Pivotal Role of Peroxisome Proliferator-activated Receptor Gamma (PPARγ) in Regulation of Erythroid Progenitor Cell Proliferation and Differentiation," *Exp Hematol* 33:857-864 (2005), which is hereby incorporated by reference in its entirety) and Kasono et al. demonstrated that some PPARγ ligands elevated platelet numbers in a mouse model of thrombocytopenia by reducing the phagocytic activity of macrophages (Kasono et al., "Thiazolidinediones Increase the Number of Platelets in Immune Thrombocytopenic Purpura Mice via Inhibition of Phagocytic Activity of the Reticulo-endothelial System," *Life Sci* 71:2037-2052 (2002), which is hereby incorporated by reference in its entirety). It was previously reported that megakaryocytes and platelets express PPARγ (Akbiyik et al., "Human Bone Marrow Megakaryocytes and Platelets Express PPARγ, and PPARγ Agonists Blunt Platelet Release of CD40 Ligand and Thromboxanes," *Blood* 104:1361-1368 (2004), which is hereby incorporated by reference in its entirety).

For this reason, the effects of PPARγ ligands on megakaryocytes were examined. The findings show that prostaglandins such as PGE$_2$, PGI$_2$, and PGF$_{2\alpha}$, which are poor activators of PPARγ, failed to enhance platelet production in Meg-01 cells. In contrast, the natural PPARγ ligand, 15d-PGJ$_2$, potently enhanced platelet production, a novel finding and contrary to the belief asserted in PCT Publ. WO 2005/041872 to Phipps et al., which is hereby incorporated by reference in its entirety.

Enhanced platelet production by 15d-PGJ$_2$ was first demonstrated by showing that two highly selective synthetic PPARγ ligands, rosiglitazone and 9,10 dihydro-15d-PGJ$_2$, do not have the same platelet enhancing effects as 15d-PGJ$_2$. Next, PPARγ independence was demonstrated by knocking-down PPARγ protein or by inhibiting PPARγ activation with the irreversible PPARγ antagonist. Under these conditions, no changes were observed in the ability of 15d-PGJ$_2$ to induce platelet production. The PPARγ-independent effects of 15d-PGJ$_2$ are likely be due to its electrophilic carbon in the cyclopentanone ring (Ray et al., "The Peroxisome Proliferator-activated Receptor Gamma (PPARγ) Ligands 15-deoxy-Delta12,14-prostaglandin J2 and Ciglitazone Induce Human B Lymphocyte and B Cell Lymphoma Apoptosis by PPARγ-independent Mechanisms, *J Immunol* 177:5068-5076 (2006); Fukushima M., "Biological Activities and Mechanisms of Action of PGJ2 and Related Compounds: An Update," *Prostaglandins Leukot Essent Fatty Acids* 47:1-12 (1992); Rossi et al., "2-Cyclopenten-1-one, A New Inducer of Heat Shock Protein 70 with Antiviral Activity," *J Biol Chem* 271:32192-32196 (1996), each of which is hereby incorporated by reference in its entirety). 9,10 dihydro-15d-PGJ$_2$, a structural analogue of 15d-PGJ$_2$, which binds to PPARγ with the same affinity as 15d-PGJ$_2$ but lacks the electrophilic carbon in the cyclopentanone ring, failed to enhance platelet production. In contrast, the electrophilic PGJ$_2$ and CDDO-Me also enhanced platelet production similarly to 15d-PGJ$_2$. It is concluded that the electrophilic properties of 15d-PGJ$_2$, PGJ$_2$, and CDDO-Me are important for their platelet enhancing effects.

The electrophilic nature of 15d-PGJ$_2$ promotes mechanisms that accompany apoptotic related events such as cytoskeletal rearrangement and ROS generation (Ray et al., "The Peroxisome Proliferator-activated Receptor Gamma (PPARγ) Ligands 15-deoxy-Delta12,14-prostaglandin J2 and Ciglitazone Induce Human B Lymphocyte and B Cell Lymphoma Apoptosis by PPARγ-independent Mechanisms, *J Immunol* 177:5068-5076 (2006); Stamatakis et al., "Identification of Novel Protein Targets for Modification by 15-deoxy-Delta12,14-Prostaglandin J2 in Mesangial Cells Reveals Multiple Interactions with the Cytoskeleton *J Am Soc Nephrol* 17:89-98 (2006); Aldini et al., "Identification of Actin as a 15-deoxy-Delta12,14-prostaglandin J2 Target in Neuroblastoma Cells: Mass Spectrometric, Computational, and Functional Approaches to Investigate the Effect on Cytoskeletal Derangement," *Biochemistry* 46:2707-2718 (2007), each of which is hereby incorporated by reference in its entirety). The data are consistent with these findings because both cytoskeletal changes (FIGS. 1G, 1I, 2E, and 3E) and ROS generation (FIGS. 5A-C) occurred after 15d-PGJ$_2$ exposure, supporting the observation that platelet production is, in part, a specialized form of apoptosis (Junt et al., "Dynamic Visualization of Thrombopoiesis Within Bone Marrow *Science* 317:1767-1770 (2007); Clarke et al., "Compartmentalized Megakaryocyte Death Generates Functional Platelets Committed to Caspase-independent Death," *J Cell Biol* 160:577-587 (2003), each of which is hereby incorporated by reference in its entirety). One recent study showed that the overexpression of scinderin, a f-actin severing protein, in Meg-01 cells led to megakaryoblast differentiation and platelet production (Zunino et al., "Expression of Scinderin in Megakaryoblastic Leukemia Cells Induces Differentiation, Maturation, and Apoptosis with Release of Platelet-like Particles and Inhibits Proliferation and Tumorigenesis," *Blood* 98:2210-2219 (2001), which is hereby incorporated by reference in its entirety). In addition, 15d-PGJ$_2$ can interact with the cytoskeleton and oxidize susceptible cysteine residues leading to f-actin depolymerization (Stamatakis et al., "Identification of Novel Protein Targets for Modification by 15-deoxy-Delta12,14-Prostaglandin J2 in Mesangial Cells Reveals Multiple Interactions with the Cytoskeleton *J Am Soc Nephrol* 17:89-98 (2006); Aldini et al., "Identification of Actin as a 15-deoxy-Delta12,14-prostaglandin J2 target in Neuroblastoma Cells: Mass Spectrometric, Computational, and Functional Approaches to Investigate the Effect on Cytoskeletal Derangement," *Biochemistry* 46:2707-2718 (2007); Gayarre et al., "Addition of Electrophilic Lipids to Actin Alters Filament Structure. *Biochem Biophys Res Commun* 349:1387-1393 (2006), each of which is hereby incorporated by reference in its entirety). Actin is a main scavenger of electrophilic lipids because of its high abundance and nucleophilic cysteine residues (Dalle-Donne et al., "Actin Cys374 as a Nucleophilic Target of Alpha, beta-unsaturated Aldehydes," *Free Radic Biol Med* 42:583-598 (2007), which is hereby incorporated by reference in its entirety). Thus, 15d-PGJ$_2$ may promote platelet production by a mechanism involving interaction with cytoskeletal proteins and f-actin depolymerization.

Figure 5A:
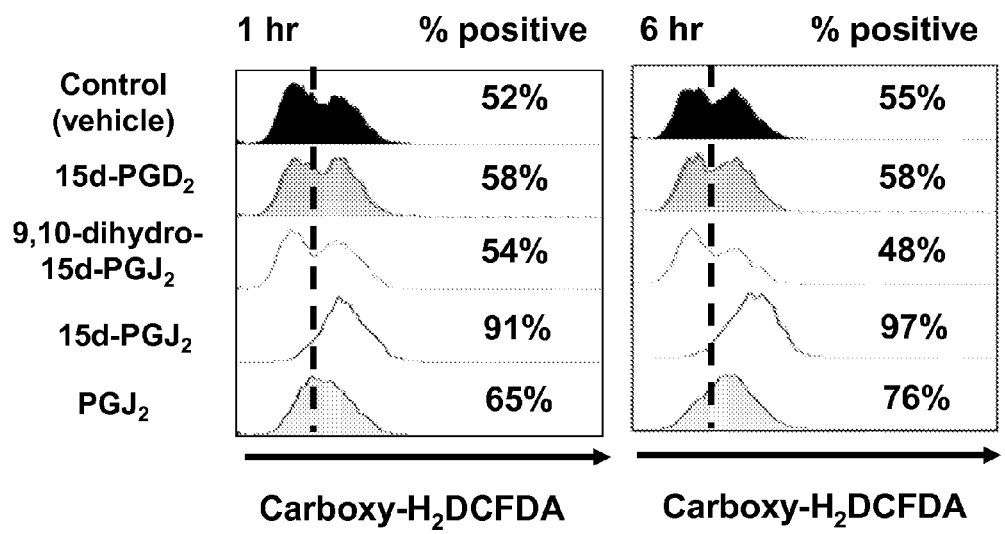
FIGS. 5A-D show that small electrophilic molecules induce the generation of ROS.
Figure 5B:
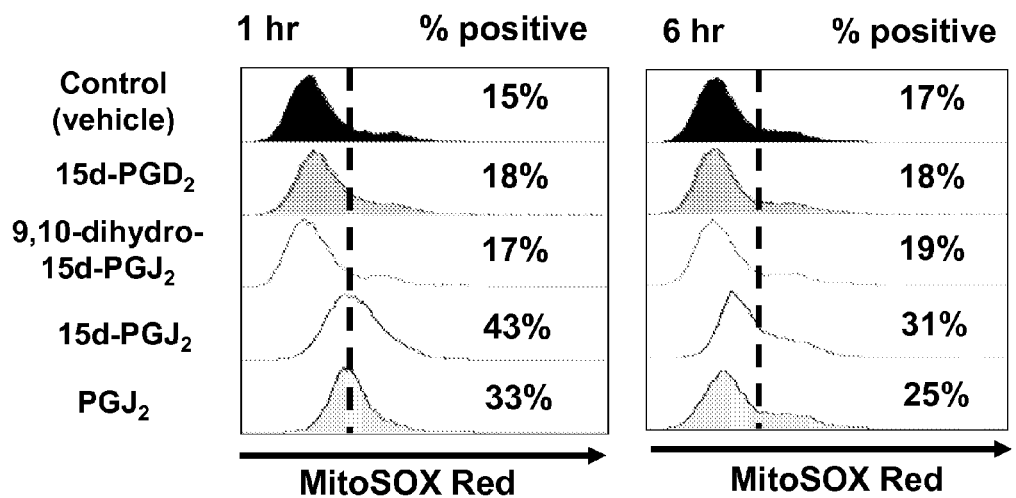
Figure 5C:
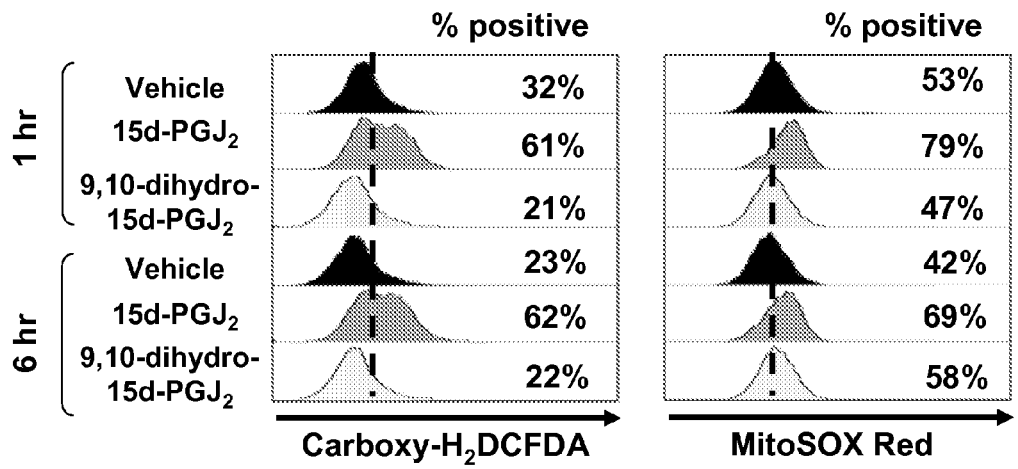
Figure 5D:
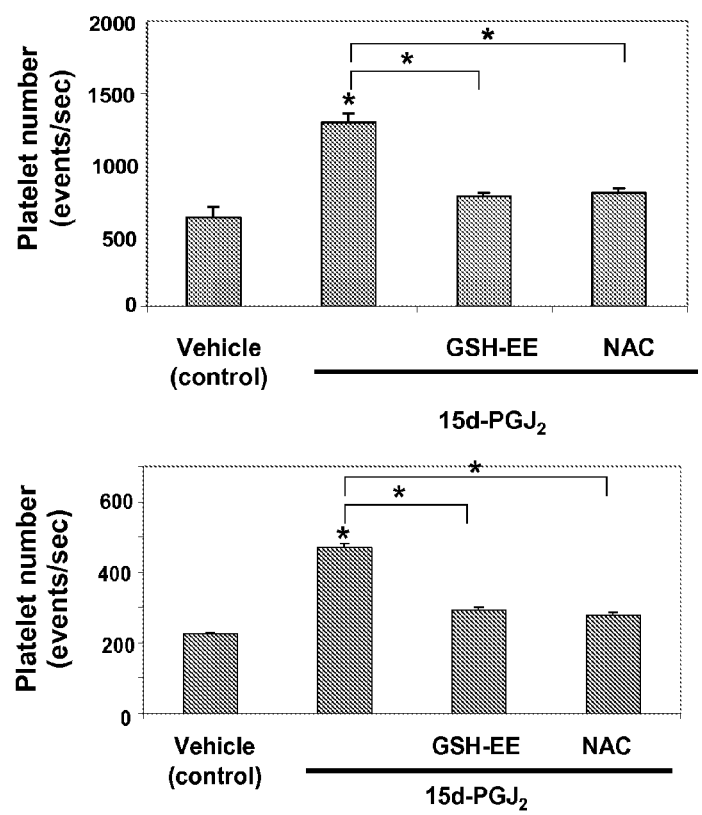

Several studies have implicated the cytoskeleton as an important regulator of the redox state of the cell, and conversely, the redox state of the cell may also influence the cytoskeleton (Cumming et al., "Protein Disulfide Bond Formation in the Cytoplasm During Oxidative Stress," *J Biol Chem* 279:21749-21758 (2004); Gourlay et al., "The Actin Cytoskeleton in Ageing and Apoptosis," *FEMS Yeast Res* 5:1193-1198 (2005), each of which is hereby incorporated by reference in its entirety. The data shows that 15d-PGJ$_2$ promotes the generation of ROS within 1 h. While it is well-known that redox status regulates cell proliferation, differentiation and survival, the role of ROS in platelet production, until now, has been unclear. It is demonstrated that ROS, and more specifically, mitochondrial superoxide, play a role in the dynamic process of megakaryocyte maturation and platelet release. Only the electrophilic molecules that generated ROS enhanced platelet production (FIGS. 5A-C). Pretreating Meg-01 cells or primary human megakaryocytes with either GSH-EE or NAC before 15d-PGJ$_2$ treatment attenuated both ROS induction and platelet formation (FIG. 5D). Interestingly, many disorders associated with oxidative stress have platelet abnormalities, such as those seen in type-2 diabetes and atherosclerosis (O'Brien et al., "The Platelet as a Therapeutic Target for Treating Vascular Diseases and The Role of Eicosanoid and Synthetic PPARγ Ligands," *Prostaglandins Other Lipid Mediat* 82:68-76 (2007), which is hereby incorporated by reference in its entirety). Further studies will be useful to determine if oxidative stress in the bone marrow, and more specifically, in the megakaryocytes, affects megakaryocyte maturation and platelet function.

15d-PGJ$_2$ and CDDO-Me not only stimulated platelet production, but also stimulated megakaryocyte maturation. While 15d-PGJ$_2$ and CDDO-Me failed to increase megakaryocyte number, megakaryocyte polyploidization was increased by both compounds. 15d-PGJ$_2$ did not significantly enhance Meg-01 ploidy until 72 h post-treatment, indicating that this is a longer-term effect and did not directly promote the platelet release that was demonstrated by 24 h. In contrast, both 15d-PGJ$_2$ and CDDO-Me enhanced primary mouse megakaryocyte ploidy by 24 h indicating that megakaryocyte maturation may play a direct role in promoting the platelet release. In addition, while 15d-PGJ$_2$ failed to promote the proliferation of megakaryocyte progenitors, the number of megakaryocytes with proplatelet extensions was significantly higher. Collectively, these results indicate that 15d-PGJ$_2$ and CDDO-Me increase platelet numbers by stimulating megakaryocyte maturation and/or subsequent proplatelet formation.

Figure 9:
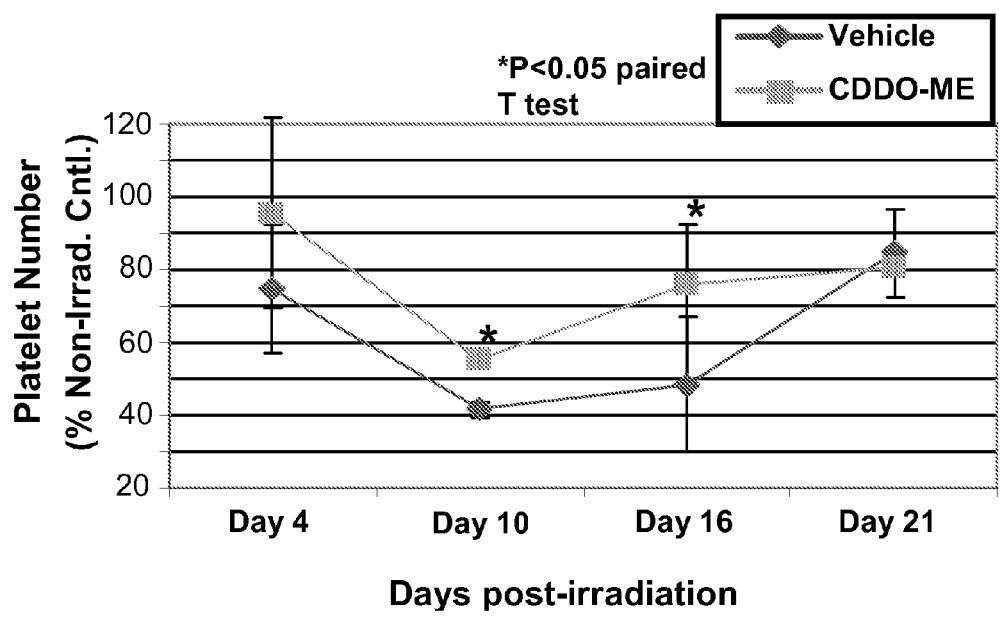
FIG. 9 is a graph illustrating the ability of CDDO-Me administration to influence platelet depletion and recovery following exposure of normal mice to 5 Gy total body irradiation (day 0). Following irradiation, mice were administered 250 μg/kg of CDDO-Me on the following four consecutive days (days 1-4), and platelet counts were measured on day 4, day 10, day 16, and day 21. CDDO-Me administration significantly improved platelet counts on days 10 and 16.

The platelet enhancing activity of 15d-PGJ$_2$ in vitro raised the possibility that it may exhibit a similar effect in vivo. As shown, 15d-PGJ$_2$ had a significant effect on enhancing platelet production (FIG. 7A), and both 15d-PGJ$_2$ and CDDO-Me accelerated platelet recovery in a mouse model of radiation-induced thrombocytopenia (FIGS. 7B, 9). A significant increase in platelet number was observed for 15d-PGJ$_2$ treatment at days 22 and 31 following radiation exposure, and for CDDO-Me treatment at days 10 and 16 following radiation exposure. The exact mechanism of action for these electrophilic compounds remains unclear.

The elevation in platelet number has potential clinical significance through promoting platelet formation in immune-mediated thrombocytopenias where megakaryocyte numbers in the marrow are normal or increased and through reducing the risk for hemorrhage during platelet recovery following myelosuppression. The latter platelet-enhancing effect may be particularly important after chemotherapy or radiation exposure, where platelet depletion is accompanied by endothelial cell damage. Another complication associated with radiation exposure is scarring of vital organs such as lung and bone marrow. Importantly, 15d-PGJ$_2$ has demonstrated significant anti-scarring activities in models of lung scarring (Burgess et al., "PPARy Agonists Inhibit TGF-beta Induced Pulmonary Myofibroblast Differentiation and Collagen Production Implications for Therapy of Lung Fibrosis," *Am J Physiol Lung Cell Mol Physiol* 288:L1146-1153 (2005), which is hereby incorporated by reference in its entirety).

CDDO-Me has demonstrated significant anti-cancer activities in glioblastomas, lung cancer, and myelogenous leukemias (Konopleva et al., "Novel Triterpenoid CDDO-Me is a Potent Inducer of Apoptosis and Differentiation in Acute Myelogenous Leukemia," *Blood* 99(1):326-335 (2002), which is hereby incorporated by reference in its entirety). CDDO-Me is a potential chemotherapeutic agent by inhibiting proliferation and disrupting intracellular redox balance leading to cell differentiation and apoptosis. The disruption of intracellular redox, along with apoptotic mechanisms such as activation of caspases and inhibition of mitochondrial membrane potential, also may promote megakaryocyte differentiation and platelet release. This indicates that CDDO-Me may be promoting platelet production by a similar mechanism.

These findings indicate that electrophilic small molecules, including prostaglandins such as 15d-PGJ$_2$ and triterpenoids such as CDDO-Me, are promising therapeutic targets for treating thrombocytopenia, and may have advantages over other thrombopoietic agents that are being developed. 15d-PGJ$_2$ and the triterpenoids like CDDO-Me are small, inexpensive to make, and can readily penetrate tissues. Additionally, 15d-PGJ$_2$ is highly conserved between species and is endogenously produced, raising the possibility that high endogenous levels of 15d-PGJ$_2$ in the bone marrow could potentially be associated with conditions characterized by high platelet counts.

Bone marrow suppression is the most common severe adverse effect following cytotoxic chemotherapy or radiation exposure and results in anemia, leukopenia and thrombocytopenia. These can be ameliorated by transfusion support, but this has unwanted side-effects including allergy, disease transmission, alloimmunization, limited availability and expense. Pharmacologic treatment with myeloid growth factors and with erythropoietin has improved our ability to accelerate myeloid and erythroid recovery, respectively. However, no comparable cytokine therapy is currently available to accelerate thrombopoiesis. The discovery that the electrophilic prostaglandin 15d-PGJ$_2$ and the electrophilic tri-terpenoid CDDO-Me exerts a potent thrombopoietic effect provides insight into the molecular mechanisms regulating both megakaryopoiesis and thrombopoiesis. This may lead to identification of new therapeutic agents to accelerate platelet recovery after marrow injury.

All of the features described herein (including any accompanying claims, abstract and drawings), and/or all of the steps of any method or process so disclosed, may be combined with any of the above aspects in any combination, except combinations where at least some of such features and/or steps are mutually exclusive.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of treating a patient for low platelet levels, the method comprising:
   administering to a patient having a low platelet level an effective amount of an electrophilic compound that is suitable to cause an increase in platelet production by megakaryocytes,
   wherein the electrophilic compound is a compound according to formula (II) or formula (III):

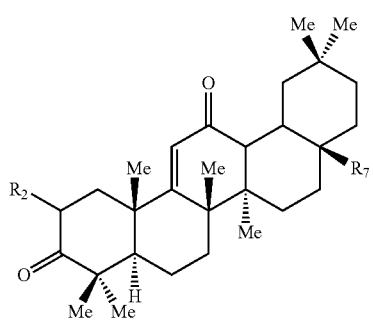

wherein $R_2$ is CN and $R_7$ is CN;

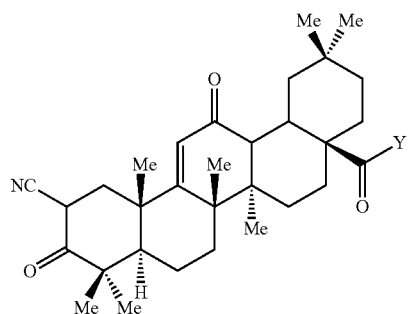

wherein Y is hydroxy, an unsubstituted $C_1$-$C_{14}$-alkoxy, an unsubstituted $C_1$-$C_{14}$-alkylamino,

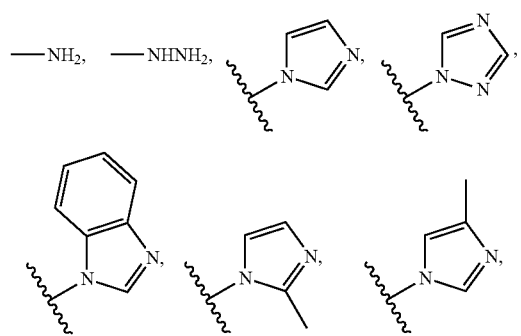

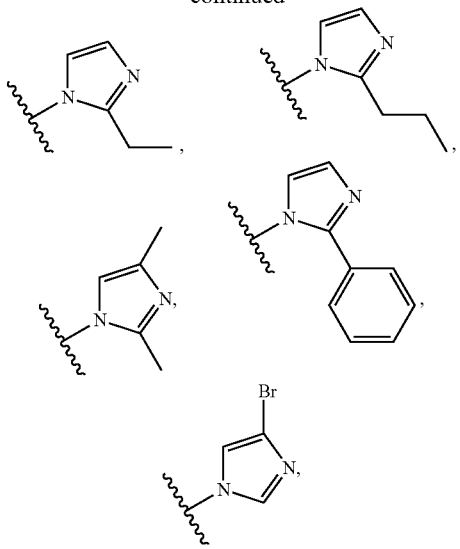

-D-Glu(OMe)$_4$, -D-Glu(OAc)$_4$, -L-Ara(OAc)$_3$, or -D-Gal-(OAc)$_4$; or a pharmaceutically acceptable salt thereof.

2. The method according to claim 1 further comprising administering an electrophilic prostaglandin selected from the group of (PG)D$_2$, PGJ$_2$, 15d-PGJ$_2$, and combinations thereof.

3. The method according to claim 1 wherein the electrophilic compound is a compound according to formula (II):

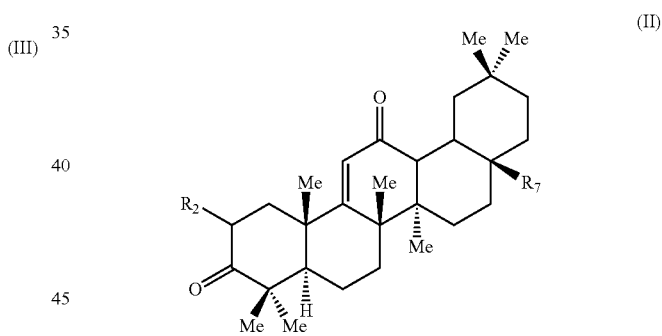

wherein $R_2$ is cyano and $R_7$ is cyano.

4. The method according to claim 1 wherein the electrophilic compound is a compound according to formula (III):

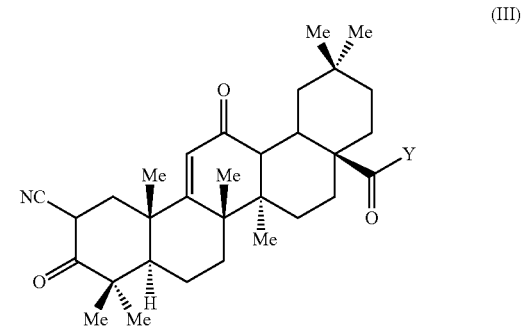

wherein Y is hydroxy, unsubstituted $C_1$-$C_{14}$-alkoxy, unsubstituted $C_1$-$C_{14}$-alkylamino,

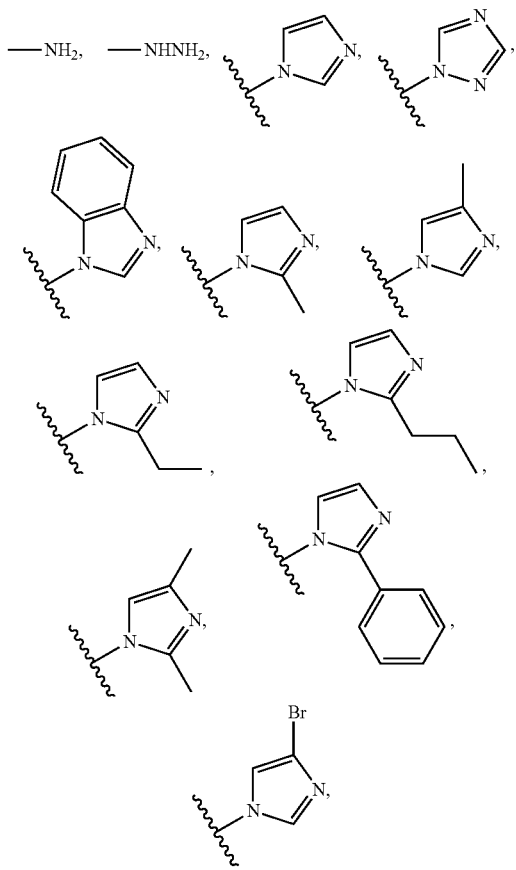

-D-Glu(OMe)$_4$, -D-Glu(OAc)$_4$, -L-Ara(OAc)$_3$, or -D-Gal-(OAc)$_4$; or a pharmaceutically acceptable salt thereof.

5. The method according to claim 1 wherein Y is hydroxy, methoxy, ethyl-amino, or

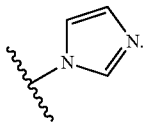

6. The method according to claim 1 wherein the electrophilic compound is present in a pharmaceutical preparation.

7. The method according to claim 1 wherein said administering is carried out orally, rectally, vaginally, parenterally, intramuscularly, intraperitoneally, intraarterially, intrathecally, intrabronchially, subcutaneously, intradermally or transdermally, intravenously, or via nasal, buccal or sublingual routes.

8. The method according to claim 1 further comprising:
    administering to the patient an effective amount of an agent that increases megakaryocyte production.

9. The method according to claim 8 wherein the agent that increases megakaryocyte production is selected from the group of thrombopoietin, megakaryocyte growth and development factor (MGDF), a combination of granulocyte colony stimulating factor (G-CSF) with either interleukin-3 or granulocyte-macrophage colony stimulating factor (GM-CSF) and optionally interleukin-6, a combination of GM-CSF and interleukin-5, pegylated recombinant human megakaryocyte growth and development factor (PEG-rHuMGDF), a small molecule c-Mpl activator, ITP-suitable peptibody, and any combinations thereof.

10. The method according to claim 8 wherein said administering the electrophilic compound and said administering the agent that increases megakaryocyte production are carried out at the same time.

11. The method according to claim 8 wherein said administering the electrophilic compound and said administering the agent that increases megakaryocyte production are carried out at different times.

12. The method according to claim 11 wherein said administering the agent that increases megakaryocyte production is carried out first, followed by said administering the electrophilic compound after a delay.

13. The method according to claim 1 wherein the patient is a radiation therapy cancer patient, a patient having an autoimmunity disorder characterized by low platelet level, or an individual exposed to ionizing radiation or a chemical in doses that cause platelet loss.

14. The method according to claim 1 wherein the patient is a chemotherapy cancer patient that receives a chemotherapeutic agent that is not an electrophilic tri-terpenoid.

15. A pharmaceutical composition or therapeutic system comprising an agent that increases megakaryocyte production and an electrophilic compound capable of inducing platelet production by megakaryocytes,
    wherein the electrophilic compound is a compound according to formula (II) or formula (III):

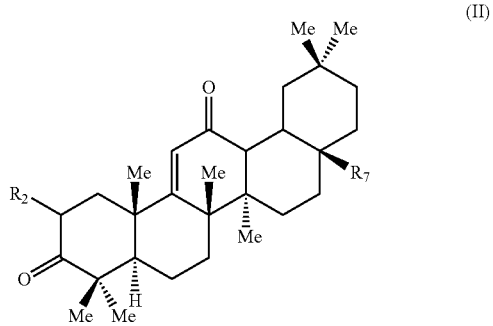

wherein R$_2$ is CN and R$_7$ is CN;

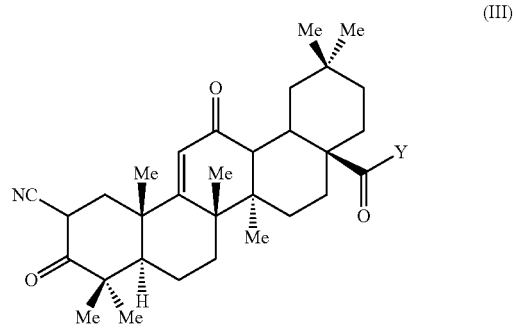

wherein Y is hydroxy, an unsubstituted $C_1$-$C_{14}$-alkoxy, an unsubstituted $C_1$-$C_{14}$-alkylamino,

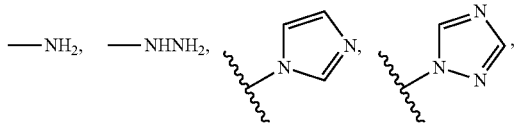

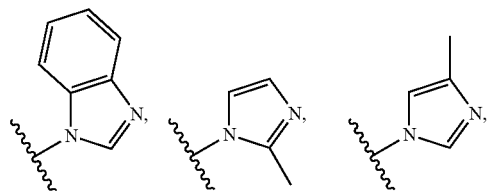

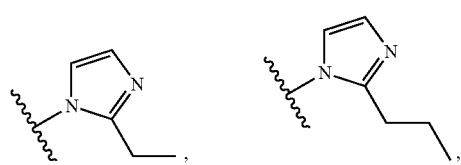

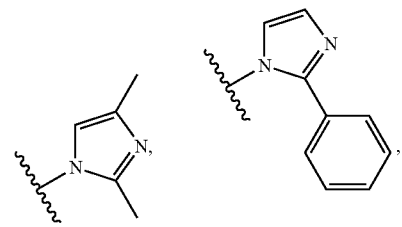

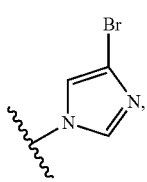

-D-Glu(OMe)$_4$, -D-Glu(OAc)$_4$, -L-Ara(OAc)$_3$, or -D-Gal-(OAc)$_4$; or a pharmaceutically acceptable salt thereof.

16. The pharmaceutical composition or therapeutic system according to claim 15 further comprising a pharmaceutically acceptable carrier.

17. The pharmaceutical composition or therapeutic system according to claim 15 in a form suitable for delivery orally, rectally, vaginally, parenterally, intramuscularly, intraperitoneally, intraarterially, intrathecally, intrabronchially, subcutaneously, intradermally or transdermally, intravenously, or via nasal, buccal or sublingual routes.

18. The pharmaceutical composition or therapeutic system according to claim 15 further comprising an electrophilic prostaglandin selected from the group of (PG)D$_2$, PGJ$_2$, 15d-PGJ$_2$, and combinations thereof.

19. The pharmaceutical composition or therapeutic system according to claim 15 wherein the electrophilic compound is a compound according to formula (II):

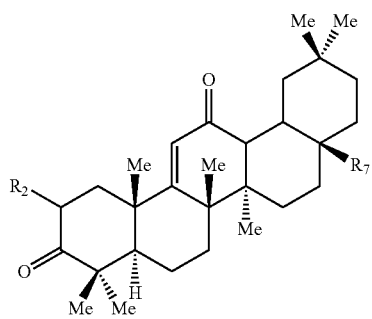

(II)

wherein R$_2$ is cyano and R$_7$ is cyano.

20. The pharmaceutical composition or therapeutic system according to claim 15 wherein the electrophilic compound is a compound according to formula (III):

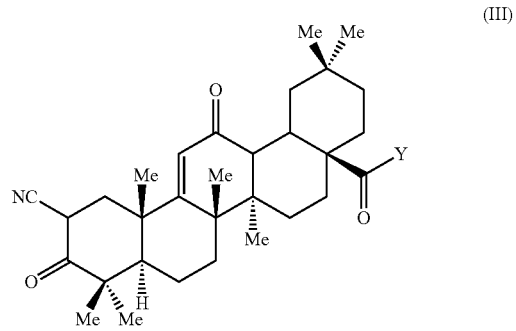

(III)

wherein Y is hydroxy, unsubstituted $C_1$ $C_{14}$-alkoxy, unsubstituted $C_1$-$C_{14}$-alkylamino,

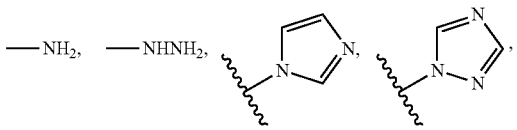

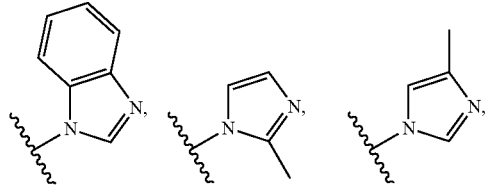

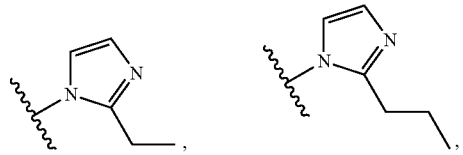

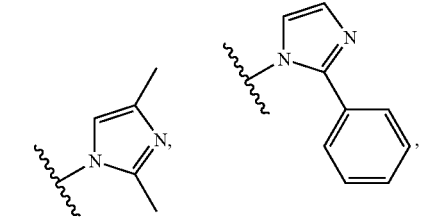

-continued

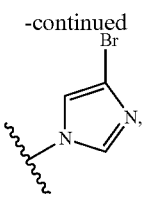

-D-Glu(OMe)₄, -D-Glu(OAc)₄, -L-Ara(OAc)₃, or -D-Gal-(OAc)₄; or a pharmaceutically acceptable salt thereof.

21. The pharmaceutical composition or therapeutic system according to claim 20 wherein Y is hydroxy, methoxy, ethylamino, or

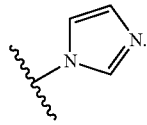 [SMILES: *n1ccnc1]

22. The pharmaceutical composition or therapeutic system according to claim 15 wherein the agent that increases megakaryocyte production is selected from the group of thrombopoietin, megakaryocyte growth and development factor (MGDF), a combination of granulocyte colony stimulating factor (G-CSF) with either interleukin-3 or granulocyte-macrophage colony stimulating factor (GM-C SF) and optionally interleukin-6, a combination of GM-CSF and interleukin-5, pegylated recombinant human megakaryocyte growth and development factor (PEG-rHuMGDF), a small molecule c-Mpl activator, ITP-suitable peptibody, and any combinations thereof.

23. The pharmaceutical composition or therapeutic system according to claim 15, wherein one or both of the agent that increases megakaryocyte production and the electrophilic compound are present in a polymeric delivery vehicle.

24. A method of treating a patient for low platelet levels, the method comprising:
administering to a patient having a low platelet level an effective amount of an electrophilic compound that is suitable to cause an increase in platelet production by megakaryocytes,
wherein the electrophilic compound is selected from the group consisting of 2-cyano-3,12-dioxooleana-1,9-dien-28-oic acid (CDDO), 2-cyano-3,12-dioxooleana-1,9-dien-28-oic imidazolide (CDDO-Im), methyl 2-cyano-3,12-dioxooleana-1,9-dien-28-oate (CDDO-Me), and 2-cyano-3,12-dioxooleana-1,9-dien-28-oic acid ethyl amide (CDDO-Ea), and a combination of any two or more thereof.

25. A pharmaceutical composition or therapeutic system comprising an agent that increases megakaryocyte production and an electrophilic compound capable of inducing platelet production by megakaryocytes, wherein the electrophilic compound is selected from the group consisting of 2-cyano-3,12-dioxooleana-1,9-dien-28-oic acid (CDDO), 2-cyano-3,12-dioxooleana-1,9-dien-28-oic imidazolide (CDDO-Im), methyl 2-cyano-3,12-dioxooleana-1,9-dien-28-oate (CDDO-Me), and 2-cyano-3,12-dioxooleana-1,9-dien-28-oic acid ethyl amide (CDDO-Ea), and a combination of any two or more thereof.

* * * * *

UNITED STATES PATENT AND TRADEMARK OFFICE
CERTIFICATE OF CORRECTION

PATENT NO. : 9,012,439 B2
APPLICATION NO. : 12/738949
DATED : April 21, 2015
INVENTOR(S) : Phipps et al.

Page 1 of 1

It is certified that error appears in the above-identified patent and that said Letters Patent is hereby corrected as shown below:

In the Specification

Column 9, lines 25-40, the chemical structure for formula (II) should read:

(II)

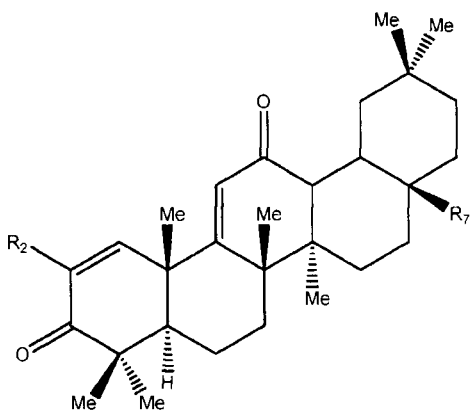

Column 10, lines 1-15, the chemical structure for formula (III) should read:

(III)

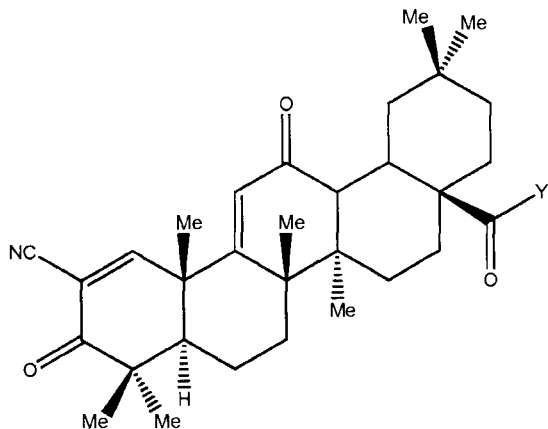

Signed and Sealed this
Fifteenth Day of September, 2015

Michelle K. Lee
*Director of the United States Patent and Trademark Office*